United States Patent
Shultz

(10) Patent No.: US 12,378,574 B2
(45) Date of Patent: Aug. 5, 2025

(54) TRANSGENIC MOUSE MODELS SUPPORTING INNATE IMMUNE FUNCTION

(71) Applicant: The Jackson Laboratory, Bar Harbor, ME (US)

(72) Inventor: Leonard D. Shultz, Bar Harbor, ME (US)

(73) Assignee: The Jackson Laboratory, Bar Harbor, ME (US)

(*) Notice: Subject to any disclaimer, the term of this patent is extended or adjusted under 35 U.S.C. 154(b) by 967 days.

(21) Appl. No.: 17/430,364

(22) PCT Filed: Feb. 13, 2020

(86) PCT No.: PCT/US2020/018033
§ 371 (c)(1),
(2) Date: Aug. 12, 2021

(87) PCT Pub. No.: WO2020/168029
PCT Pub. Date: Aug. 20, 2020

(65) Prior Publication Data
US 2022/0136002 A1 May 5, 2022

Related U.S. Application Data

(60) Provisional application No. 62/805,257, filed on Feb. 13, 2019.

(51) Int. Cl.
*C12N 15/85* (2006.01)
*A01K 67/0275* (2024.01)
*C12N 5/0783* (2010.01)

(52) U.S. Cl.
CPC ...... *C12N 15/8509* (2013.01); *A01K 67/0275* (2013.01); *C12N 5/0636* (2013.01); *A01K 2217/05* (2013.01); *A01K 2227/105* (2013.01); *A01K 2267/03* (2013.01); *C12N 2517/02* (2013.01)

(58) Field of Classification Search
CPC ............ A01K 67/0278; A01K 67/0275; A01K 2267/03; A01K 2267/0387; C12N 15/8509
See application file for complete search history.

(56) References Cited

U.S. PATENT DOCUMENTS

| 2012/0094312 A1 | 4/2012 | Di Santo et al. |
| 2012/0157667 A1 | 6/2012 | Chen et al. |
| 2022/0127639 A1 | 4/2022 | Keck |

FOREIGN PATENT DOCUMENTS

| JP | 2012-531896 A | 12/2012 |
| WO | WO 2017/205756 A1 | 11/2017 |
| WO | WO 2020/008066 A1 | 1/2020 |
| WO | WO 2020/168029 A1 | 8/2020 |
| WO | WO 2022/011007 A1 | 1/2022 |
| WO | WO 2023/122138 A1 | 6/2023 |

OTHER PUBLICATIONS

Mackarehtschian K, Hardin JD, Moore KA, Boast S, Goff SP, Lemischka IR. Targeted disruption of the flk2/flt3 gene leads to deficiencies in primitive hematopoietic progenitors. Immunity. Jul. 1995;3(1):147-61. doi: 10.1016/1074-7613(95)90167-1. PMID: 7621074. (Year: 1995).*
Witt RG, Kreger EM, Buckman LB, Moradi PW, Ho PT, Derderian SC, Tsai P, Baker C, Schramm N, Cleary R, Garcia JV, MacKenzie TC. Systemic multilineage engraftment in mice after in utero transplantation with human hematopoietic stem cells. Blood Adv. Jan. 5, 2018;2(1):69-74. (Year: 2018).*
Invitation to Pay Additional Fees mailed May 7, 2020 for International Application No. PCT/US2020/018033.
International Search Report and Written Opinion mailed Jul. 6, 2020 for International Application No. PCT/US2020/018033.
International Preliminary Report on Patentability mailed Aug. 10, 2021 for International Application No. PCT/US2020/018033.
Blunt et al., Defective DNA-Dependent Protein Kinase Activity is Linked to V(D)J Recombination and DNA Repair Defects Associated with the Murine scid Mutation. Cell. Mar. 10, 1995;80(5):813-23. doi: 10.1016/0092-8674(95)90360-7.
Cao et al., Defective Lymphoid Development in Mice Lacking Expression of the Common Cytokine Receptor gamma Chain. Immunity. Mar. 1995;2(3):223-38. doi: 10.1016/1074-7613(95)90047-0.
Do et al., IL-15 produced and trans-presented by DCs underlies homeostatic competition between CD8 and γδ T cells in vivo. Blood. Jun. 18, 2009;113(25):6361-71. doi: 10.1182/blood-2008-12-192997. Epub Apr. 20, 2009.
Durai et al., Altered compensatory cytokine signaling underlies the discrepancy between $Flt3^{-/-}$ and $Flt31-/-$ mice. J Exp Med. May 7, 2018;215(5):1417-1435. doi: 10.1084/jem.20171784. Epub Mar. 23, 2018.
Fu et al., Improving CRISPR-Cas nuclease specificity using truncated guide RNAs. Nat Biotechnol. Mar. 2014;32(3):279-284. doi: 10.1038/nbt.2808. Epub Jan. 26, 2014. (Author Manuscript, 18 pages).
GENBANK Submission; NIH/NCBI, Accession No. NC_000019. 10. Grimwood et al., Mar. 26, 2018. 2 pages.
Gordon et al., Integration and stable germ line transmission of genes injected into mouse pronuclei. Science. Dec. 11, 1981;214(4526):1244-6. doi: 10.1126/science.6272397.

(Continued)

*Primary Examiner* — Fereydoun G Sajjadi
*Assistant Examiner* — Qinhua Gu
(74) *Attorney, Agent, or Firm* — Wolf, Greenfield & Sacks, P.C.

(57) ABSTRACT

Provided herein, in some aspects, is a NOD.Cg-Prkdc$^{scid}$ Il2rg$^{tm1wjl}$/SzJ (NOD scid gamma or NSG™) mouse comprising a nucleic acid encoding human FLT3L and an inactivated mouse Flt3 allele, methods of producing the mouse, and methods of using the mouse.

20 Claims, 13 Drawing Sheets
Specification includes a Sequence Listing.

(56) References Cited

OTHER PUBLICATIONS

Gossler et al., Transgenesis by means of blastocyst-derived embryonic stem cell lines. Proc Natl Acad Sci U S A. Dec. 1986;83(23):9065-9. doi: 10.1073/pnas.83.23.9065.
Greiner et al., SCID Mouse Models of Human Stem Cell Engraftment. Stem Cells. 1998;16(3):166-77. doi: 10.1002/stem.160166.
Harms et al., Mouse Genome Editing Using the CRISPR/Cas System. Curr Protoc Hum Genet. Oct. 1, 2014;83:15.7.1-27. doi: 10.1002/0471142905.hg1507s83. (Author Manuscript, 39 pages).
Hsu et al., DNA targeting specificity of RNA-guided Cas9 nucleases. Nat Biotechnol. Sep. 2013;31(9):827-32. doi: 10.1038/nbt.2647. Epub Jul. 21, 2013. (Author Manuscript, 17 pages).
Inui et al., Rapid generation of mouse models with defined point mutations by the CRISPR/Cas9 system. Sci Rep. Jun. 23, 2014;4:5396(1-8). doi: 10.1038/srep05396.
Jaenisch, R., Germ line integration and Mendelian transmission of the exogenous Moloney leukemia virus. Proc Natl Acad Sci U S A. Apr. 1976;73(4):1260-4. doi: 10.1073/pnas.73.4.1260.
Klein et al., Flt3 ligand expands $CD4^+FoxP3^+$ regulatory T cells in human subjects. Eur J Immunol. Feb. 2013;43(2):533-9. doi: 10.1002/eji.201242603. Epub Dec. 5, 2012.
Low et al., Simple, Efficient CRISPR-Cas9-Mediated Gene Editing in Mice: Strategies and Methods. Methods Mol Biol. 2016;1438:19-53. doi: 10.1007/978-1-4939-3661-8_2.
Makino et al., Breeding of a Non-Obese, Diabetic Strain of Mice. Exp. Animal. Jan. 1980;29(1):1-13. doi: 10.1538/expanim1978.29.1_1.
Mooney et al., Selective Expression of Flt3 within the Mouse Hematopoietic Stem Cell Compartment. Int J Mol Sci. May 12, 2017;18(5):1037(1-19). doi: 10.3390/ijms18051037.
Oliveros et al., Breaking-Cas-interactive design of guide RNAs for CRISPR-Cas experiments for ENSEMBL genomes. Nucleic Acids Res. Jul. 8, 2016;44(W1):W267-71. doi: 10.1093/nar/gkw407. Epub May 10, 2016.
Palucka et al., Cancer immunotherapy via dendritic cells. Nat Rev Cancer. Mar. 22, 2012;12(4):265-77. doi: 10.1038/nrc3258. (Author Manuscript, 30 pages).
Shultz et al., Humanized mice for immune system investigation: progress, promise and challenges. Nat Rev Immunol. Nov. 2012;12(11):786-98. doi: 10.1038/nri3311. Epub Oct. 12, 2012. (Author Manuscript, 27 pages).
Shultz et al., Human Lymphoid and Myeloid Cell Development in NOD/LtSz-*scid IL2R gamma*$^{null}$ Mice Engrafted with Mobilized Human Hemopoietic Stem Cells. J Immunol. May 15, 2005;174(10):6477-89. doi: 10.4049/jimmunol.174.10.6477.
Shultz et al., Humanized mice in translational biomedical research. Nat Rev Immunol. Feb. 2007;7(2):118-30. doi: 10.1038/nri2017.
Shultz et al., Humanized Mouse Models of Immunological Diseases and Precision Medicine. Mamm Genome. Jun. 2019;30(5-6):123-142. doi:10.1007/s00335-019-09796-2. (Author Manuscript, 34 pages).
Shultz et al., Multiple defects in innate and adaptive immunologic function in NOD/LtSz-scid mice. J Immunol. Jan. 1, 1995;154(1):180-91.
Tsapogas et al., The Cytokine Flt3-Ligand in Normal and Malignant Hematopoiesis. Int J Mol Sci. May 24, 2017;18(6):1115(1-23). doi: 10.3390/ijms18061115.
Tzelepis et al., A CRISPR Dropout Screen Identifies Genetic Vulnerabilities and Therapeutic Targets in Acute Myeloid Leukemia. Cell Rep. Oct. 18, 2016;17(4):1193-1205. doi: 10.1016/j.celrep.2016.09.079.
Zriwil et al., Direct role of FLT3 in regulation of early lymphoid progenitors. Br J Haematol. Nov. 2018;183(4):588-600. doi: 10.1111/bjh.15578. Epub Sep. 14, 2018.
Du et al., Using CRISPR/Cas9 for Gene Knockout in Immunodeficient NSG Mice. Methods Mol Biol. 2019;1874:139-168. doi: 10.1007/978-1-4939-8831-0_8. Abstract.
Iwabuchi et al., Introduction of Human Flt3-L and GM-CSF into Humanized Mice Enhances the Reconstitution and Maturation of Myeloid Dendritic Cells and the Development of $Foxp3^+CD4^+$ T Cells. Front Immunol. May 28, 2018;9:1042. doi: 10.3389/fimmu.2018.01042.
Li et al., A novel Flt3-deficient HIS mouse model with selective enhancement of human DC development. Eur J Immunol. May 2016;46(5):1291-9. doi: 10.1002/eji.201546132. Epub Mar. 1, 2016.
Vaidya et al., Enhanced development of functional human innate immune cells in a novel mouse FLT3$^{null}$ NSG mouse strain expressing human FLT3L. J Immunol. May 1, 2020;204(1 Suppl):223.24. Abstract.
Willinger et al., Improving human hemato-lymphoid-system mice by cytokine knock-in gene replacement. Trends Immunol. Jul. 2011;32(7):321-7. doi: 10.1016/j.it.2011.04.005. Epub Jun. 21, 2011.
Anselmi et al., Development and function of human dendritic cells in humanized mice models. Mol Immunol. Sep. 2020;125:151-161. doi: 10.1016/j.molimm.2020.07.005. Epub Jul. 17, 2020.
Ding et al., FLT3-ligand treatment of humanized mice results in the generation of large numbers of $CD141^+$ and $CD1c^+$ dendritic cells in vivo. J Immunol. Feb. 15, 2014;192(4):1982-9. doi: 10.4049/jimmunol.1302391. Epub Jan. 22, 2014.
Guil-Luna et al., Humanized Mouse Models to Evaluate Cancer Immunotherapeutics. Annu Rev Cancer Biol. Mar. 2021;5(1):119-36. doi: 10.1146/annurev-cancerbio-050520-100526.
Yaguchi et al., Human PBMC-transferred murine MHC class I/II-deficient NOG mice enable long-term evaluation of human immune responses. Cell Mol Immunol. Nov. 2018;15(11):953-962. doi: 10.1038/cmi.2017.106. Epub Nov. 20, 2017.

\* cited by examiner

SEQUENCE LISTING

```
<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 1
gaacagcuug gugcauucg                                                      19

<210> SEQ ID NO 2
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 2
gauggucacc aacgcugac                                                      19

<210> SEQ ID NO 3
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 3
ccaacctgaa ctgtatggag atag                                                24
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
ccacagggaa agccactaaa                                                    20

<210> SEQ ID NO 5
<211> LENGTH: 1500
<212> TYPE: DNA
<213> ORGANISM: Mus musculus

<400> SEQUENCE: 5
atcccccagt gctggtgacc ttgaacacag ggtctgccct gagcagtgct gacagcctgt        60
tagctgtcat tttgaagcat ttcctgaagg aaacttacct tatcattgca gctgtaaaga       120
agaaggccct gctgttgtca gaaaggagga aaagtgtactt catgagttgt tcggaacaga      180
catcagatgc tgtgctagaa atgcactggg ccgcgaatgc accaagctgt tcaccatagg       240
taatggggga ctgtcggcta tgtgtcctta gtgacggttc ctaagggacc ggtgatagct       300
tctgtgtggg taatcattcc acttcagaaa gatgatggaa agttatactg aaatccgaat       360
ctagatcgaa tagtccacat tctgacataa aagcaattga acacacaggt atggccaagc       420
ttggtggccc gggcttttaa tccttctttc ataggacttt gatttgattc aatttgatt       480 gatttgattt gacttaggtg ctgggctcaa acccagggac tcagagcatc tgctttgcca       540
ctgagttcca ctccagatct tttgcaccac tttatttatt tatttattgt gtgtgtgtat       600
acacacatta aatacacaca catacacaca cacacacaca cacacacaca cacacacaca       660
cacacacaca cacgctacag catgtaatgt ggatgtcagg ttctcttctt gtcatatggg       720
gcccctggat caaattcagg tcagtctggc agcggcaggc acctccaccc actgagccat       780
cttgatgccc cgttcatacc atttacaatg taacactgta gattctgtaa gggaggattt       840
ctgcaacaaa gggtattcca tctcgagtgg gtggttttac tctgtcgctt tttttttttt       900
agttttgtgc tgctctgtga ctccaggtct tctccaggcc agcctctttt accctgatct       960
tctcagctct gcattgtttg gcttgattag tgatggcagg gatgctgaca ccattgcttt      1020
tcaaaacgtt tgcgacactt ctgagctgag gcaaaagtttt taaaaaaaa gatgtgctttt     1080 ttttttttt ttttttgtctt ctttgggata ttttttatctt ctagatctaa accaggctcc     1140
tcagagcaca ctgccccagt tattcctgaa agtgggggaa cccttgtgga tcaggtgtaa      1200
ggccatccat gtgaaccatg gattcgggct cacctgggag ctggaagaca aagccctgga     1260
ggaggtaaca gcgcccaccc gtggtgttta ccgtaagctc tcagcgtggg ctggaaaccc      1320
ggaatacaga ctcccctttc attaatactc agggcagcta ctttgagatg agtacctact     1380
ccacaaacag gaccatgatt cggattctct tggcctttgt gtcttccgtg ggaaggaacg     1440
acaccggata ttacacctgc tcttcctcaa agcaccccag ccagtcagcg ttggtgacca     1500

<210> SEQ ID NO 6
<211> LENGTH: 442
<212> TYPE: DNA
<213> ORGANISM: Artificial Sequence
<220> FEATURE:
<223> OTHER INFORMATION: Synthetic polynucleotide

<400> SEQUENCE: 6
```

| | |
|---|---|
| ccaacctgaa ctgtatggag atagcttgtc tatggggaaa aaaaatcacc aaataaaata | 60 |
| aaatctaaaa tattaaataa taaagtaata ctgtaacatt atcctaatta gatacagagt | 120 |
| agctagctgg tccctgcaga ttccaggctg atacagttg agttaatttt tcatctgctc | 180 |
| ttttcttcca tccctaaaaa tatactttgt aacttcatcc cctaaacata ctgggtcccc | 240 |
| ccaccccatc ctaggtaacg ggctcacgaa atttggggtt ggttggtttg tttgttttta | 300 |
| atgctgtcct ggaactcgct gtgtagattg gttggccttg aactcacaga aatctaccag | 360 |
| catctgcctc cccagtgctg ggattaaagg cacaggccac caagcttgac tctgcttgtg | 420 |
| tctttagtgg cttctccctgt gg | 442 |

<210> SEQ ID NO 7
<211> LENGTH: 13880
<212> TYPE: DNA
<213> ORGANISM: Homo sapiens
<400> SEQUENCE: 7

| | |
|---|---|
| gatccctgtg ctcctccgag tggcacagga aacttggctg atagaggcgc tctctccatg | 60 |
| catcctccac catccactcc ccggtcccctt agacttccat tcagaagtga cacctgtcac | 120 |
| ctccacccct atgtgactgg ccaaagtgag tgtggccatg tccgagttcc ccaggatggg | 180 |
| acctcgaatc ctcctgctgg gggggtgggg gcagcagatg tttcaggaca gtctgccacg | 240 |
| gatcagatgg gtgagcaaga gattcaggat gggcgtgatg ggtcacacct gtaatcccag | 300 |
| cattttggga ggccgaggca ggctgatcac ctgaggtcag gagttcgaga tcagcctggc | 360 |
| caacatagtg aaaacctcgtc tctactaaaa atacaaaaat tagccgggca tggtggcacg | 420 |
| cacctgcaat tccagctact tgggagcctg aggcacaaga attgcttaag cccaggaggc | 480 |
| ggaggttgcc gtgagccgag actgtgccac tgcactccag cctgggcaac agagtgagac | 540 |
| cccatctaaa aaaaaaaaat gcttcagaga ttcagagatc cacagatgtg aagagagct | 600 |
| tctattttgt ctcatgtacc acctcacccc tcagtttgga gttggagaag ccgaggctta | 660 |
| gagaggtcaa ggggctggcc aagctcccac agtgataaag ctagtgctag ggcgacacct | 720 |
| gccaggccca atgtgacaag atgcatcctg agtcctgtgt gccaagcctt ggcggggcaa | 780 |
| agttggggcc cggaggacgg taagacacag caactgcgag ttcccagaga cagatccggg | 840 |
| ttccagcccc agctcaccat gcactgggcg tgccacccag ggagtcagcc ccactgcagc | 900 |
| ccccgctgcg gggcgtccgg agaacgcgcc atctgcggcg tgagcggccg cctctcacca | 960 |
| ccaggggggcg cgctccgcct gggcccagat tccacccctt gactgtctcc cccaaaaat | 1020 |
| ttcctttcac tttcggtctc tggctgtcac ccggcttggc cccttccaca cccaactggg | 1080 |
| gcaagcctgg tgcgtgagga gacttggact ctaggtcccc aaggggcgga gccagggtcc | 1140 |
| ccactcctgg ggcaggggga gcagagggtg gggggctggg ttcccgggtc cctaacctgg | 1200 |
| ggagggttct ggggaccaga cgtcgaggtt cttagaagtg gagatgaaga gttttcaccg | 1260 |
| taactggggc agacgcagga agcctggggg aggaaggggc ggaaactcag ccacatcaat | 1320 |
| gggacgcggg aggggcgggg aggcaaaggg gcgggcaggg caggggctgg ggcatgaggg | 1380 |
| tccgagactt gttcttctgt cccttccaag acccggcgac aggaggcatg aggggccccc | 1440 |
| ggccgaaatg acagtgctgg cgccagcctg gagcccaaca gtgcgtaaac cccagggaca | 1500 |
| agatcagggg agagggggagg cacaatgtca ggatggggca gagatgaggg gagatggacg | 1560 |
| ggagaacaga tggacagatg acgaggaaat aggagggga atggacagat gtgagggag | 1620 |
| atggatagga gaggagacgg acagaggagg gggagatgga cagaggatgg ggagatggac | 1680 |

```
agaggagggg gagatagagg agagggagat agagaggagt gggagatgga caggagcggg      1740
gagatggaca gaggaggggg agatggacag aggagagggc agatgaacag aggagaggga      1800
gataaagagg agggaggtgg acaggaggag ggagatggac agagaagggg gagatggaca      1860
gaggtggggg agatggacag gagggaagat ggagaggagg gggtatggac agaggagagg      1920
ggagatggac aggaggggga gatggacaga ggagagggag atgaagagga ggggaggtg       1980 gacaggagga gggagacgga cagaggagag gaagagagac agaggagggg ggagatggac      2040
agaggagggg gagatggaca gaaaagggg gagatggaca gaggagaggg aaggtggaca       2100
gagccaagaa caaatgaaga ggacgtggac caagatcaag agagaagcag gcaacagtgg      2160
tgtagaaggc agagggaggg acagagctgg aggaacccgg gcgaggaaac cagacgtgaa      2220
gatgaggtgg ttggagagag accagcagag tgggggagat ggggagagag aggggtgggg      2280
cagaggggga tgcaaactgg acagcattgg accagaggca gagagaaacc gggaaagaca      2340
ggcagagatg gggccatgtc tccagaaagt gtggaagagg cagaaggaca cccagggaag      2400
gaggagcggg gaagacagaa cagtacaggt gggaagcccg gaggagggg ctgtgtgtgg       2460 aacagcagag ggctccccca gcacccgctc ccctgcagac ctatctcctc ctgctgctgc      2520
tgctgagctc gggactcagt gggacccagg actgctcctt ccaacacagc ccatctcct      2580 ccgacttcgc tgtcaaaatc cgtgagctgg tgagcggcgc tgccccggac ccctcatgt      2640 gatccccctt ccccccactt tttttttaa gtagagatgg ggtctctctc cctgtgtttc      2700
ccagggtggc cttgaactcc tgggctcaag cgatcctccc accttggcct cccaaagtgc      2760
tggaattaca ggcgtgagcc actgtgctta ggggtgtcat ccctttttaa gggcaaggtt      2820
ctgtggcttc ttctgggctc cccctctctt ggtcttgtcc ctctctctct ggatctctgc      2880
tgccacctct gggtccccac agttctgttt ctcgctgttt tcagccaggc ctgatcctgt      2940
tttctcccgc agtctgacta cctgcttcaa gattacccag tcaccgtggc ctccaacctg      3000
caggacgtaa gtcatgttgg gagggacctg ggatggaggt ggggaccaca gactcaagat      3060
gctccaccga ggcgagtgga taaccaggcc ctcccctccc caaacccagg aatcagagtc      3120
ctcagcccct cctccctcag acccaggagc cccggcccag cccctcctcc ctcagaccca      3180 gcagcccgt gcccagctcc tccctcagac ccgtgggttc tccctctag gaggagctct        3240 gcgggggcct ctggcggctg gtcctggcac agcgctggat ggagcggctc aagactgtcg      3300
ctgggtccaa gatgcaaggc ttgctggagc gcgtgaacac ggagatacac tttgtcacca      3360
aatgtgcctt tcaggtcagc cctcaactta ggggacaagt gaggggaggg agatgccttc      3420
ctacgaatta gaagtaaagc tccactaggc cttattggcg atttggacca tagccaccca      3480
acgaaggtag agcgagaagc gccacccctgc agagccctgt tcctacagaa caacacgtcc      3540
ccaggcaccg gtgatgggga gcagtctggt cccattctgg ggccccggtt tcctaggcca      3600
tgatgaaggg tgccactgag gggttcttcc cccaaaaaaa aacagggaga gaagggtct       3660 ctaaactgag gaggccgggc gtggtggctc actcctgtaa tcctagcact ttgggaggct      3720
gaggtgggcg gatcacttga ggtcaggagt ttgagaccag cctggccaac atgatgaaat      3780
cccggctgta ctaaaaatac aaaaattagc cgggcatggt ggctcaggag ctgaggcac       3840 aggaatcgct tgaacccggg agccagaggc tgcagtgagc cgagatcatg ccactgcact      3900
ccagcctggg agacagagtg aaactgtctc aaaaacaaaa caaacaaaca aaacctctc       3960 tctgagggct gggtgcagtg gctcacacct gtaatcccag cactttcgga ggccaaggtg      4020
```

```
ggaggattat ttgagcccag gagttcaaga ccagcccggg taacacagtg aaacctcatc    4080
tctgcacaaa aataaaaata aattagccag gcatggtggt gcccacctgt ggtcccagct    4140
actcagaagg ctgaggtggg aggatcactt gagccctgga ggtcgaggct gcgatgagct    4200
atgattgggc cactgcactc cagcttgagc gacagagcaa gaccctgtct caaaacatag    4260
aataggccgt gtatggtggc tcacgactgt aatcccagca ctttgggagg ctgaggcggg    4320
tggattgcct gagctcagga gttcgagacc agcctcggca acgtgatgaa aaccatctct    4380
actaaaatac aaaaacaaaa ttagccaggc atggtggtgg gcacctgtag tcccagctac    4440
ttgggagact gaggcaggag aattgcttga acccaggagg cagaggttgc agtgagccga    4500
gatcacacca ctgccctcca gcctgggcga cagagcaaga ctccatctcc aaaaaaataa    4560
aaataaaata aaagcctggg tacagtggct cacgcctgta atcccagcac tttgggagcc    4620
cgaggcgggc agatcacgag gtcaggagtt tgagaccacc ctggccaatg tggtgaaacc    4680
ccgtctctac taaaaataca aaaattagct gggcatggtg gcgcgcgcct gtagtcccag    4740
ctactcagga ggctgaggca gaattccttg aacccgggag gtagaagttg cagtaagccg    4800
agatcgtgcc actgtactcc agccagggtg acagagcaag actctgtccc caaaaaataa    4860
ataaataata aagtaacttt gggaggccga ggcgggcgag tcacctgagg tcaggagttc    4920
gagaccagcc tggccaacat agagaaaccc cgtttctact aaaaaatata aataaataaa    4980
taaataaata aataggctgg gcacggtggc tcacgcctgt aatcccacac tttgggaggc    5040
cgaggcgggc ggatcacaag gtcaggagat caagaccatc ctggctaaca caatgaaacc    5100
ccatctctac taaaaataca aacaattagc cgggcgtggt ggcaggcgcc tgtagtccca    5160
actacctggg aggctgaggc aggtgaatgg cgtgaaacca ggaggcggag cttgcagtga    5220
gccgagattg cgccactgta ctccagcctg gcaacagag cgagactctg tcttaaaaat    5280
aaataaataa ataaatatgg ccaagcacgg tggctcatgc ctacaatccc agcactttgg    5340
gaggccaagt gggcagatc acctgaggtc aggagttcga gaccagcctg ccaacatgg    5400 agaaaccccg tctctactac aaatacaaaa aatagctggg catggtggtg gcacctata    5460 gtcccaacca ctgaggaggc tgaggcagga gaatcacttg aacctgggag gcagaggttg    5520
catttcacca ctccagcctg gcaacagag tgagactcta tctcaaaaaa aaattaatta    5580
attaaataaa taaactctga gagccagagc tcactgggcc ctgttgctgg gcatcgccag    5640
cagggaaggg cctttggcct gcggaggggc ggtgggggga tgacgtggtg gtgacgtctc    5700
cctcccctgc tcccagcccc cccccagctg tcttcgcttc gtccagacca acatctcccg    5760
cctcctgcag gagacctccg agcagctggt ggcgctgaag ccctggatca ctcgccagaa    5820 cttctccccgg tgcctggagc tgcagtgtca gcccggtaaa ggcttccagg cacccccact    5880
ccttcccctc ctgtcctcac ggccgctcct cctctctgca cagtgcatcc cagacccat    5940 cttttctcata ttggttgtga caagggcaag cttattcctc tttctggagc tcagtttacc    6000 aattttttt ttttttttt gagacggagt ctcgcactgt cgcccaggct ggagtgcagt    6060
ggcgtgatct tggctcactg caagctccgc ctctcgggtt catgccattc tcctgcctca    6120
gcctcccaag tagctgggac cacaggcgcc cgccaccaca cccggctaat ttttgtatt    6180 tttagtagag acggggtttt accgagttaa accaggatgg tctcgatctc ctgaccttgt    6240
gatccacctg ccttggcctc ccaaagtgct gggattacag gcgtgagcca cagtgcccag    6300 cctaccttt tttttttt tttttttgag atggagtctt gctctgtccc ccaggctgga    6360 gtgcagggt gctatctcgg ctcactgcaa gctctgcctc ctgggttcac gccattctct    6420
```

```
tgcctcagcc tccccagcag ctgggactac aggcgcctgc cacctcacgc ggctaatttt      6480
tttttttgta tttttagtag agacggtgtt tcaccgtgtc agccaggatg gtctcgatct      6540
cctgacctcg tgatctgccc gcctcggcct cccaaagtgc taggattaca gatgtgagcc      6600
accgcgccca gcctattgtt ttttttttct aagtcggagt cttgctctgt cgcccaggct      6660
ggagtgcagt ggcgcaatct tggctcactg caacctccat ctccagggtt caagcgaatc      6720
ttctgcctca gccttccgag tacctgggat tacagatgcg cataccatgc ctggctagtt      6780
tttgtgtttt tagtagagat gggttttcac catgttggcc aggctggtct tgaactcctg      6840
acctcaagtg atccacccac cttggcctcc caaagtgctg ggattatagg cgtgagccac      6900
cgcgctcagc ctattcactc atttaatttg tgacagtctg atgaggtagg tacaatgatt      6960
atcctagttt tacagatgag caaactgagg cacagagagg ccaagcagcc catccaaggt      7020
cacacagcca gtggcagcca ggcctctctt tccttcctta ccccagccct tctccttggt      7080
cacccagcct cctctttctc ccagactcc tcaaccctgc caccccatg gagtccccgg       7140 cccctggagg ccacagcccc gacagccccg cagccccctc tgctcctcct actgctgctg      7200
cccgtgggcc tcctgctgct ggccgctgcc tggtgcctgc actggcagag gacgcggcgg      7260
aggacacccc gccctgggga gcaggtgagc aggctgggaa gaggggtga ggggccgag       7320 agggtggccc acttgtggct gacactttgg ggcccacagg tgcccccgt ccccagtccc       7380 caggacctgc tgcttgtgga gcactgacct ggccaaggcc tcatcctggt gagtccttcc      7440
tgggctatgg ggcctggact ttgtgtctgc aggttgggag ggtcactagg aggccatgga      7500
agggtggtga gcagtggagg ggcaggggca gctctaggtg cagaaagacc cctctggggc      7560
caggcgcggt ggctcacgcc tgtaatccca gcactttggg aggccgaggc gggtggatca      7620
cttgaggtca ggagttcaag accagcctgg ccaacatggc aaaccccagt ctctactaaa      7680
aatacaaaaa ttaactgggc atagtggtgt gtgcctgtaa tcccagctac tcaggaggct      7740
gaggaaggag aattgcttga acccaggagg cggaggttgc agtgagccga gattgcgcca      7800
ctggactcca gcctgagtga cagagctaga ctccgtctca aaaaaaaaaa aaaaaagaa       7860 aaggaaagac ccctctgggg ccacggagac agactggaga ccaagccgga ggctgtggga      7920
aggcccaggg tgaggaccat gactgagcca gggctgggac catgggatgg agtggagtgg      7980
atgggcagag agtcagggt cagagatcag gaggaccgg cctggggcct gacaggcttg        8040
agttggcaca gatagccctg gtccagtgat ggggtggaca ggggggaacc tggggaggaa      8100
gtcagattag ggaaagacat ggagctcact ggggacctga aggagcaagg ggccctgggg      8160
agatctgtgg atgtgggagt ttgcaagcct cctgggacag gaaggaaatg gcattccaga      8220
aagagggaac tgcctttgga agccctttgg tatgagaaag ctcagggtgt tccagtaact      8280
tgggccagcg tggggcagca aggagccatg ggaggtgtga gaggaggaa aggagctggg       8340 aacaggtgtg gagggtgcag gcaggtaggc aggtgggcca ggaggaaga aggaggggag       8400 gccccagcgg gtcccctaac atttcaaatc taacattttg tagtaattgc tcgcacatat      8460
agtgccttgg taatgcaggc ctcatgtggg gctggcttgc ttgctttatt ttttttgag      8520 atggactctc actctgtcac ccaggctgga gtgcagtggg ggatcttgg ctcactgcaa       8580 cctccacctc ccaggttcaa gcaattctcc tgcctcagcc tcccaagtag ctgggattac      8640
aggcgcccgc caccatgcct ggctaatttt ttgtatttt agtagagatg gggtttcgcc       8700
atgttggcca ggctggtctc aaactcctga tctcagctga tccgcccgcc tcagcctccc      8760
```

-continued

```
aaagtgctgg gatgacaggt gtgagccact gttcctggcc catgctgggc tttccacaaa    8820
tgaactcact tccttgagaa gttcgtgcca ttatgatccc aaggcataga gaggtaaata    8880
atttgccaaa agtcacacag ctcaagggtg acaaccaaga tttgacttca ggttgtcttt    8940
ttttttttt tgagatggag tcttgctctg tcgcccaggc tgtagtgcag tggcatgatc    9000
tcggctcact gcagccccg cctcccaggt tcaagtgatt ctcctgcctc agcctctgga    9060
gtagctggga ttacaggtac ccaccaccac actcggctaa ttttgtatt tgtagtagag    9120
acggggtttc accatgttgg ccaggctggt ctcgaactcc tgaccttagc tgatccgccc    9180
gcctcagcct cccaaagtgc tgggattaca ggcatgagcc accacgcccg gcctcgagtt    9240
tgtcttgatc cagcatctgt gcccttcact ctgctgcctc agtttcctga tctgtacaaa    9300
aggctctaat aatagtcctt ccaccatagg gttgttatgg ggtgaagtga agtgacacag    9360
gcaaggctct tagagcaacg cagtggaaac ggcatgtgag ccacctgtgc gattttcact    9420
ttcctggtag ccacatttt ttttttttt tcctgagatg gagtctcact ctgtcgccag    9480
gttgaagtgc agtggtgtga tctcagctca ctgcaacctc cacctcccgg gttcaagcga    9540
ttctcctgct tcagtctacc gagtagctgg gattacaggc acgcgccatc acgcccggct    9600
aatttttgt gttttagta gagacaaggt ttcaccatgt tggtcaggct ggtctcgaac    9660
tcctgacctc atgatccacc cgcctcagcc tcccaaagtg ctgggattac aggcgtgagc    9720
caccgcgccc ggggtcacag ttttaaaaa aggaaaaga agcaggtaac tttattttat    9780
gcagtatatc caaaatgttg ttatttcaac atgtaatcag tatttctcaa tgattaatga    9840
gacattaatc agttggaatc attcatcatt ttgggatatt ttacattctt ttgtcatact    9900
aagccttcag catccaacgt atagtttatt tatttattta tttttccttt tgagatggat    9960
tctgctctg tcacccaggc tggagtgcag tggcgcgatc tcagctcact gcaacctcgg   10020
actccctggt tcaggcgatt ctcctgcctc agcctcccga gtacctggga ttacgccacc   10080
acacccagct aatttttgta ctttagtag agaccgggtt tcaccatgtt ggccaggatg   10140
atctccatcc cctgacctcg tgatccgccc gcctcagcct cccaaagtgc tggattacaa   10200
gtgtaagcca ccgcgcccag cccagacaat aaatttttat cagaaatgct tcatctatat   10260
ttaaatttca tgaaatttac agttgccaaa agtagactca catagtcaag ttgttcaaaa   10320
catacattaa accagcctgg gccacatggt gaaaccccat ctctacaaaa aatttaaaa   10380
agtagctggg tgtggtggca catgcctgca gtcccagcta cttaggaggc aaagtaggag   10440
gattgcttga gcccaggagg tcgaggctgc agtgagccct gattgtgcca ctgcactcca   10500
gcctgggtga gagagcaaga ccctgtctca aaaacaaaa accacacag aagagtttag   10560
aatcccagtt gctatctctg ggaatcatca tgattgctaa gaccggtatc tatccaacaa   10620
caacaaaaat aattagtgca ctccagcctg ggcaatagag ggagactctg tctcaaaaaa   10680
aaaaaaaaaa aaaaaaaaaa gatcaaagac cagtatctaa attgctctgt cgcccagggt   10740
ggagtgcagt ggcacgatct cggctcactg caacctccgc ctcccgggtt caagtgattc   10800
tcctgcctca gcctcccag tagcttggac tacaggcgcg tgccaccaca cccagctaat   10860
ttttgtattt ttagtagagg tagggtttca ctatgtttgc caggattgtc tcgatctctt   10920
gacctcgtga tctgcccgcc tcagcctccc aaagtgctgg gattataggc gtgagccacc   10980
acgcccagcc tatcttttt ttttttttta agaaaggta atacattgag cagttttcct   11040
cccaacctag tccctgtcca atctgttcc tgtcttaaat ttatttta ttataatttt   11100
tttttttt tttttttgtg agacagactt ttgctcttgt tagccaggct ggagtgcagt   11160
```

```
ggtgctatct tgactcacgg caacctccac ctcccaggtt caagcgattc tcctgcctca    11220
gcctctggag tagcttggat tacaagcgcc tgccaccacg cccaactaat ttagtgtatt    11280
tttagtagag acggggtttc ttttgttgtt gttgttgttt ttgagacgga gtctcactct    11340
attgcccagg ctggagtgca acggcacgat ctcggctcac tgcaacatct gcctcccggg    11400
ttcaagcgat tctactgcct cagcctcctg agtagctggg attacaggca cacaccacca    11460
cacctggcta attttgtat ttttagtaga gatggggttt caccatattg gccaggctga    11520
tctcgaactc ctgacctcgt gatctgcccg ccttgacctc ccaaagtgat aggattacag    11580
ccatgagccg ccctgcccaa ctaatacctg atattaattt tattgtatct cacccagcat    11640
ggtggctcac acctgtaact ccttggcaga tcgcttgagc ctaagagttc aagaccagct    11700
tgggcaacat ggtgaaaccc cgtctctact aaaaatataa aaatgagctg ggcatggtgg    11760
cgtgcacccg taatcccagc taactcagga ggctgaggca ggaagaatgg cttgaacccg    11820
ggaggcagag gctgcagtga gctgagatca tgccactgca ttccagcctg aaacagagca    11880
agactgtctc aaaagaagtt taagtccagc ctcaaactcc tggactcaag tgatcctcct    11940
gcctcagcct cctgagtagt gcaccggccc catctcaagt gttcagtatt cacatgtggc    12000
ttgttactcc cgtattaaag agcaaaaata gagaacgttt cttttctttt tttttctttt    12060 ttttttttt tttgagatgg gagtttcgct cttgtcgccc aggctggagt gcaatggcac    12120
gatcttggct caccgcaacc tctgcctccc aggttcaagc gattctcctg cctcagcctc    12180
ccaagtagct gggattacag acatgcacca ccatgcctag caaattttgt ttttgttttt    12240 gttttttct tttgagacag acttttgctt ttattgccaa ggctggagtg caatggtgca    12300
atctcgactc actgcaacct ccgcctcccg ggttcaagca attctcctgc ctcagctaat    12360
tttgtagttt tagtagaaac ggtttctcca tgttagctag gctggtctca aactcccaac    12420
ctcaggtgat ccgcccgcct cgacctccta aagtgctgga attacaggcg tgagccactg    12480
tgcctggccc taattttgta tttttagtag agatggggtt tctccctgtt ggtcaggctg    12540
gtctcaaact cccaacctaa ggtgatccac cagcctcagc ctcccaaact gctgggatta    12600
taggcatgag ccaccgcgcc cggggaaata tagggaacat ttctatcatg gccacgttct    12660
cttggacagc aatgccctag cacatagtaa gcgcttgctg ggaatggagt tgttttgggc    12720
ataaatctgt ggcccgcccc aagctaagct actttccctc tcctctctca gcggagcctt    12780
aaacaacgca gtgagacaga catctatcat cccattttac aggggaggat actgaggcac    12840
acagagggga gtcaccagcc agaggatgca tagcctggac acagaggaag ttggctagag    12900
gccggtccct tccttgggcc cctctcattc cctccccaga atggaggcaa cgccagaatc    12960
cagcaccggc cccatttacc caactctgta caaagccctt gtccccatga aattgtatat    13020
aaatcatcct tttctaccag ctctggccag gtctgtctat ggatgggtgt gaatggggta    13080
gttttgattt cagaatcttg gttttttgaat tgcaatgcaa tgtttcattc aatacgtgtt    13140
ttctgaggtc ccctggagcc ccgggccggc gctgggcaat gtcagagcct ggatttgagt    13200
cagaaccagc ccaggtgccc caggtctcct tggctatgga cgagaagaca agggattcag    13260
cgagcctggg tgcaggatgc cataggctac tatggagata aaacagaggc agtgtgaggg    13320
gcaactcacc caggcaggga gagcagagag gctttccaga gccaaatggc attgcgatgg    13380
tgacaagcca gatttggagg gggtggggag ggcatcctgg gcaagggacc cagctgaagc    13440
aaaggccgac agtccagaaa gtgagaagtt cctctgagga acgctcagtg gattggtgca    13500
```

```
gccaggcaac tagaagccat tccttgatcc actcttagag cccctgggga agaccacctc    13560
catctgtttt acagatggat aaactgaggc ccagataagg ccaagggttt ctccaggtca    13620
cagtgaagtc gaccagacac aggaatccaa atctctaagc ctagaatggg caaggctccg    13680
gggctcacgc cggtaatccc agcactttgg gaggccgaaa cgggaggatc gcttgagccc    13740
aggagttcga gatcagcctg gccaacatgt cagactcccc ccgttcccgg gccacaacaa    13800
aatatatata tatatatata ttagccaggc atggtggcgc gcccctgtag tccaagttac    13860
tcgagaggct gaggcaggag                                                13880
```

TRANSGENIC MOUSE MODELS SUPPORTING INNATE IMMUNE FUNCTION

RELATED APPLICATIONS

This application is a national stage filing under 35 U.S.C. § 371 of international application number. PCT/US2020/018033, filed Feb. 13, 2020, which claims the benefit under 35 USC § 119 (e) of U.S. provisional application No. 62/805,257, filed Feb. 13, 2019, each of which is incorporated by reference herein in its entirety.

GOVERNMENT LICENSE RIGHTS

This invention was made with government support under grant number 1R01132963 awarded by National Institutes of Health. The government has certain rights in the invention.

BACKGROUND

Signaling through the fms-related tyrosine kinase 3 (FLT3) receptor supports survival, proliferation, and differentiation of hematopoietic progenitor cells and dendritic cells (DCs) (1, 2). Human DCs are necessary to present antigen to human T cells and are required for the development of a robust human immune response (4). Mature human DCs also produce interleukin 15 and other factors that support development of natural killer (NK) cells and other components of a human innate immune system (5).

SUMMARY

Provided herein, in some embodiments, is an immunodeficient NOD.Cg-Prkdc$^{scid}$ Il2rg$^{tm1Wjl}$/SzJ (NSG™) mouse (a "NOD scid gamma" mouse), comprising a nucleic acid encoding human FLT3L (e.g., comprising a human FLT3L transgene) and an inactivated mouse Flt3 allele. Although the NSG™ mouse supports human hematopoietic stem cell (HSC) engraftment, it exhibits impaired development of human HSCs into dendritic cell (DC) populations (3). To provide a mouse model that supports development of human HSCs into DC populations, a transgenic NSG™ mouse expressing human FLT3L (NSG™-Tg(Hu-FLT3L)) was generated. Unexpectedly, however, engraftment of human HSCs was significantly lower in the NSG™-Tg(Hu-FLT3L) mouse compared with the NSG™ control. In an effort to understand the phenotype observed in the NSG™-Tg(Hu-FLT3L) mouse, the endogenous mouse receptor for FLT3L—Flt3—was knocked out. Surprisingly, engraftment with human HSCs of this transgenic line, referred to herein as NSG™ Flt3$^{null}$-Tg(Hu-FLT3L), results in (1) significantly increased percentages of both human CD3$^+$ T cells and human CD33$^+$ myeloid cells, (2) increased percentages of human CD123$^+$ plasmacytoid dendritic cells, CD56$^+$ human natural killer (NK) cells, CD14$^+$ human monocyte macrophages, and CD11C$^+$ HLA-DR$^+$ human myeloid dendritic cells, and (3) support of mucosal engraftment of human CD45$^+$ cells in the small intestines. Without being bound by theory, the decreased human HSC engraftment NSG™-Tg(Hu-FLT3L) may have been a consequence of human FLT3L activating, through the host mouse FLT3 receptor, the host mouse DCs and possibly other innate immune mouse components.

Thus, some aspects of the present disclosure provide a NSG™ mouse comprising a nucleic acid encoding human FLT3L and an inactivated mouse Flt3 allele (NSG™ Flt3$^{null}$-Tg(Hu-FLT3L)). This mouse model supports development of HSCs into many different cell types of the human innate immune system, including dendritic cells.

In some embodiments, the mouse comprises a genomic modification that inactivates the mouse Flt3 allele. The genomic modification, in some embodiments, is in at least one region of the mouse Flt3 allele selected from coding regions, non-coding regions, and regulatory regions. In some embodiments, the genomic modification is in at least one coding region of the mouse Flt3 allele. For example, the genomic modification may be in exon 6, exon 7, and/or exon 8. In some embodiments, the genomic modification is selected from genomic deletions, genomic insertions, genomic substitutions, and combinations thereof. For example, the genomic modification may be a genomic deletion. The mouse Flt3 allele may comprise, for example, a genomic deletion of nucleotide sequences in exon 6, exon 7, and exon 8.

In some embodiments, the nucleic acid sequence of SEQ ID NO: 5 has been deleted from the mouse Flt3 allele.

In some embodiments, the modified mouse Flt3 allele comprises the nucleic acid sequence of SEQ ID NO: 6.

In some embodiments, the nucleic acid encoding human FLT3L comprises a human FLT3L transgene. In some embodiments, the human FLT3L transgene comprises a nucleic acid sequence of SEQ ID NO: 7. In some embodiments, the mouse expresses human FLT3L. The human FLT3L may be expressed, for example at a level of at least 10,000 pg/ml. In some embodiments, the human FLT3L is expressed at a level of 10,000 pg/ml to 30,000 pg/ml. For example, the human FLT3L may be expressed at a level of 15,000+/−1000 pg/mL to 17,000+/−100 pg/ml.

In some embodiments, the mouse expresses mouse FLT3L. In some embodiments, the mouse FLT3L is expressed at a level of at least 2,000 pg/ml. For example, the mouse FLT3L may be expressed at a level of 5,000 pg/ml to 10,000 pg/ml. In some embodiments, the mouse FLT3L is expressed at a level of 6,000 pg/ml to 8,000 ml.

In some embodiments, the mouse does not express a detectable level of mouse FLT3. In some embodiments, a detectable level of mouse FLT3 expressed by the mouse is less than 1,000 pg/ml.

In some embodiments, the mouse lacks a detectable number of CD135$^+$ multipotent progenitor cells.

In some embodiments, the mouse further comprises human CD34$^+$ hematopoietic stem cells. The human CD34$^+$ hematopoietic stem cells, in some embodiments, are from human umbilical cord blood, bone marrow, or mobilized peripheral blood.

In some embodiments, the mouse comprises a population of human CD45$^+$ cells. The population of human CD45$^+$ cells comprises, in some embodiments, human CD45$^+$/CD3$^+$ T cells and/or human CD45$^+$/CD33$^+$ myeloid cells.

In some embodiments, the population of human CD45$^+$ cells comprises an increased percentage of human CD45$^+$/CD3$^+$ T cells, relative to a NOD scid gamma control mouse or a NOD scid gamma-Hu-FLT3L control mouse. For example, the percentage of human CD45$^+$/CD3$^+$ T cells in the mouse may be increased by at least 25%, at least 50%, or at least 100%.

In some embodiments, the population of human CD45$^+$ cells comprises an increased percentage of human CD45$^+$/CD33$^+$ myeloid cells, relative to a NOD scid gamma control mouse or a NOD scid gamma-Hu-FLT3L control mouse. For example, the percentage of human CD45$^+$/CD33$^+$ myeloid cells in the mouse may be increased by at least 25%, at least 50%, or at least 100%.

In some embodiments, the mouse comprises an increased percentage of human CD123+ plasmacytoid dendritic cells, relative to a NOD scid gamma control mouse or a NOD scid gamma-Hu-FLT3L control mouse. For example, the percentage of human CD123+ plasmacytoid dendritic cells in the mouse may be increased by at least 25%, at least 50%, or at least 100%.

In some embodiments, the mouse comprises an increased percentage of human CD56+ natural killer cells, relative to a NOD scid gamma control mouse or a NOD scid gamma-Hu-FLT3L control mouse. For example, the percentage of human CD56+ natural killer cells in the mouse may be increased by at least 25%, at least 50%, or at least 100%.

In some embodiments, the mouse comprises an increased percentage of human CD14+ monocyte macrophages, relative to a NOD scid gamma control mouse or a NOD scid gamma-Hu-FLT3L control mouse. For example, the percentage of human CD14+ monocyte macrophages in the mouse may be increased by at least 25%, at least 50%, or at least 100%.

In some embodiments, the mouse comprises an increased percentage of human CD11C+ HLA-DR+ myeloid dendritic cells, relative to a NOD scid gamma control mouse or a NOD scid gamma-Hu-FLT3L control mouse. For example, the percentage of human CD11C+ HLA-DR+ myeloid dendritic cells in the mouse is increased by at least 25%, at least 50%, or at least 100%.

In some embodiments, the mouse exhibits mucosal engraftment of human CD45+ cells in the small intestines of the mouse.

Other aspects of the present disclosure provide a method comprising sublethally irradiating the mouse, and injecting the mouse with human CD34+ hematopoietic stem cells.

In some embodiments, the method further comprises administering to the mouse an agent of interest. In some embodiments, the method further comprises assessing an effect of the agent on human immune cells in the mouse.

In some embodiments, the method further comprises the human immune cells are selected from T cells, dendritic cells, natural killer cells, and macrophages.

Yet other aspects of the present disclosure provide a method comprising injecting a pronucleus of a NOD.Cg-Prkdc$^{scid}$ Il2rg$^{tm1Wjl}$/SzJ (NOD scid gamma) mouse with a nucleic acid encoding human FLT3L, producing a NSG Tg(Hu-FLT3L) mouse, and inactivating a mouse Flt3 allele in the NSG Tg(Hu-FLT3L) mouse.

Further other aspects of the present disclosure provide a method comprising inactivating a mouse Flt3 allele in a NOD.Cg-Prkdc$^{scid}$ Il2rg$^{tm1Wjl}$/SzJ (NOD scid gamma) mouse to produce a NSG Flt3$^{null}$ mouse, and injecting a pronucleus of the NSG Flt3$^{null}$ mouse with a nucleic acid encoding human FLT3L.

Still other aspects of the present disclosure provide a method comprising breeding female mice homozygous for Prkdc$^{scid}$, homozygous for Il2rg$^{tm1Wjl}$, homozygous for Flt3$^{null}$, and homozygous for a human FLT3L transgene with male mice homozygous for Prkdc$^{scid}$ hemizygous for the X-linked Il2rg$^{tm1Wjl}$, homozygous for Flt3$^{null}$, and homozygous for a human FLT3L transgene to produce progeny mice.

Further still, some aspects of the present disclosure provide a NOD.Cg-Prkdc$^{scid}$ Il2rg$^{tm1Wjl}$/SzJ cell comprising a nucleic acid encoding human FLT3L and an inactivated endogenous Flt3 allele.

Yet other aspects of the present disclosure a transgenic rodent comprising a cell comprising a nucleic acid encoding human FLT3L and an inactivated endogenous Flt3 allele. In some embodiments, the transgenic rodent is a transgenic mouse.

Some aspects of the present disclosure provide a gRNA targeting mouse Flt3, optionally wherein the gRNA targets exon 6 or exon 8 or mouse Flt3. In some embodiments, the gRNA comprises the sequence of SEQ ID NO: 1. In some embodiments, the gRNA comprises the sequence of SEQ ID NO: 2.

Also provided herein is a mouse oocyte comprising any one of the gRNAs described herein. In some embodiments, the mouse oocyte is fertilized.

Some aspects further provide a mouse oocyte comprising a first gRNA targeting exon 6 of mouse Flt3 and a second gRNA targeting exon 8 of mouse Flt3, optionally wherein the mouse oocyte is fertilized.

A mouse oocyte, in some embodiments, further comprises Cas9 mRNA and/or Cas9 protein.

A mouse oocyte, in some embodiments, further comprises a human FLT3L transgene.

DETAILED DESCRIPTION

NSG™ Flt3$^{null}$-Tg(Hu-FLT3L) Mouse

Figure 1:
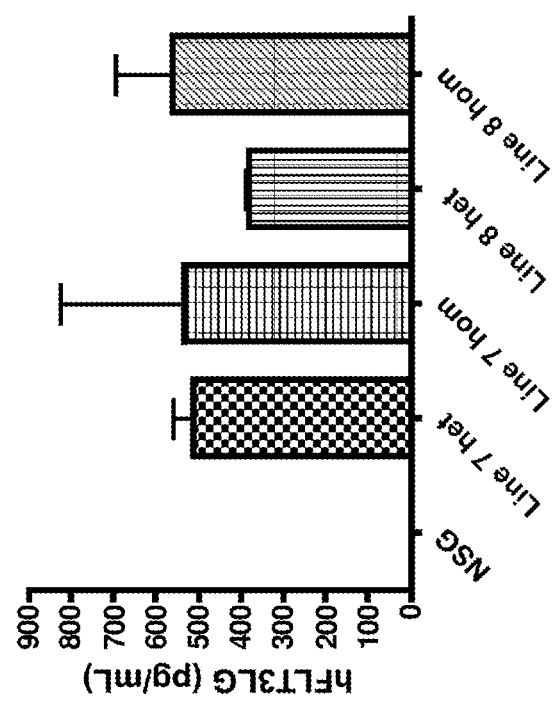
FIG. 1 shows human FLT3L levels in sera from NSG™-transgenic mice expressing human FLT3L (NSG™-Tg(Hu-FLT3L) that are hemizygous (labeled as Het) or homozygous (labeled as hom) for human FLT3L from founder lines 7 and 8. Each bar represents values from 3-4 female or male mice at 5 to 15 weeks of age.

The present disclosure provides a NOD.Cg-Prkdc$^{scid}$ Il2rg$^{tm1Wjl}$/SzJ (NSG™) Mouse comprising a nucleic acid encoding human FLT3L and an inactivated mouse Flt3 allele. This mouse is referred to herein as a NSG™ Flt3$^{null}$-Tg(Hu-FLT3L) mouse.

The NSG™ mouse is an immunodeficient mouse that lack mature T cells, B cells, and natural killer (NK) cells, is deficient in multiple cytokine signaling pathways, and has many defects in innate immunity (see, e.g., Shultz L D et al. *Nat. Rev. Immunol.* 2007; 7 (2): 118-130; Shultz L D et al. 2005; *J. Immunol.* 174 (10): 6477-89; and Shultz L D et al. *J. Immunol.* 1995; 154 (1): 180-91). The NSG™ mouse, derived from the non-obese diabetic (NOD) mouse strain NOD/ShiLtJ (see, e.g., Makino S et al. *Jikken Dobutsu* 1980; 29 (1): 1-13), include the Prkdc$^{scid}$ mutation (also referred to as the "severe combined immunodeficiency" mutation or the "scid" mutation) and the Il2rg$^{tm1Wjl}$ targeted mutation. The Prkdc$^{scid}$ mutation is a loss-of-function mutation in the mouse homolog of the human PRKDC gene—this mutation essentially eliminates adaptive immunity (see, e.g., Greiner D L et al. 1998; *Stem Cells* 16 (3): 166-177; and Blunt T et al. 1995; *Cell* 80 (5): 813-23). The Il2rg$^{tm1Wjl}$ mutation is a null mutation in the gene encoding the interleukin 2 receptor gamma chain (IL2Rγ, homologous to IL2RG in humans), which blocks NK cell differentiation, thereby removing an obstacle that prevents the efficient engraftment of primary human cells (Shultz L D et al. 2005; Greiner et al. 1998; and Cao X. et al. *Immunity* 1995; 2 (3): 223-38). A loss-of-function mutation, as is known in the art, results in a gene product with little or no function. By comparison, a null mutation results in a gene product with no function. An inactivated allele may be a loss-of-function allele or a null allele.

The NSG™ Flt3$^{null}$-Tg(Hu-FLT3L) mouse provided herein comprises a nucleic acid encoding human FLT3L. FLT3L (e.g., NC_000019.10; chromosome:GRCh38:19: 49473607: 49486831:1) is a cytokine and growth factor that stimulates the production of immune cells (e.g., B cells and T cells) by binding and activating the FLT3 receptor (see, e.g., Klein O. et al. *Eur J Immunol.* 2013; 43(2): 533-539). FLT3L is important for the development of steady-state dendritic cells. In some embodiments, the nucleic acid encoding human FLT3L comprises a human FLT3L transgene. Surprisingly, the data described herein show that human FLT3L is capable of binding mouse FLT3, which, without being bound by theory, may activate innate mouse immunity. Thus, in some embodiments, the NSG™ mouse provided herein comprises a nucleic acid (e.g., DNA) encoding human FLT3L and an inactivated mouse Flt3 allele.

A nucleic acid may be DNA, RNA, or a chimera of DNA and RNA. In some embodiments, a nucleic acid (e.g., DNA) encoding human FLT3L comprises a gene encoding FLT3L. A gene is a sequence of nucleotides (DNA or RNA) that encodes a molecule (e.g., a protein) having a function. A gene may be endogenous (occurring naturally in a host organism) or exogenous (transferred, naturally or through genetic engineering, to a host organism). An allele is one of two or more alternative forms of a gene that arise by mutation and are found at the same locus on a chromosome. A gene, in some embodiments, includes a promoter sequence, coding regions (e.g., exons), non-coding regions (e.g., introns), and regulatory regions (also referred to as regulatory sequences). As is known in the art, a promoter sequence is a DNA sequence at which transcription of a gene begins. Promoter sequences are typically located directly upstream of (at the 5' end of) a transcription initiation site. An exon is a region of a gene that codes for amino acids. An intron (and other non-coding DNA) is a region of a gene that does not code for amino acids.

A mouse comprising a human gene is considered to comprise a human transgene. A transgene is a gene exogenous to a host organism. That is, a transgene is a gene that has been transferred, naturally or through genetic engineering, to a host organism. A transgene does not occur naturally in the host organism (the organism, e.g., mouse, comprising the transgene). In some embodiments, a mouse as provided herein, comprises a FLT3L transgene, such as a human FLT3L transgene. In some embodiments, the human FLT3L transgene is integrated into the mouse genome. In some embodiments, the human FLT3L transgene comprises the nucleic acid sequence of SEQ ID NO: 7.

An inactivated allele is an allele that does not produce a detectable level of a functional gene product (e.g., a functional protein). In some embodiments, an inactivated allele is not transcribed. In some embodiments, an inactivated allele does not encode a functional protein. Thus, a mouse comprising an inactivated mouse Flt3 allele does not produce a detectable level of functional FLT3. In some embodiments, a mouse comprising an inactivated mouse Flt3 allele does not produce any functional FLT3.

In some embodiments, a mouse (e.g., a NSG™ Flt3$^{null}$-Tg(Hu-FLT3L) mouse) comprises a genomic modification that inactivates the mouse Flt3 allele. A modification, with respect to a nucleic acid, is any manipulation of the nucleic acid, relative to the corresponding wild-type nucleic acid (e.g., the naturally-occurring nucleic acid). A genomic modification is thus any manipulation of a nucleic acid in a genome, relative to the corresponding wild-type nucleic acid (e.g., the naturally-occurring nucleic acid) in the genome. Non-limiting examples of nucleic acid (e.g., genomic) modifications include deletions, insertions, "indels" (deletion and insertion), and substitutions (e.g., point mutations). In some embodiments, a deletion, insertion, indel, or other modification in a gene results in a frameshift mutation such that the gene no longer encodes a functional product (e.g. protein). Modifications also include chemical modifications, for example, chemical modifications of at least one nucleobase. Methods of nucleic acid modification, for example, those that result in gene inactivation, are known and include, without limitation, RNA interference, chemical modification, and gene editing (e.g., using recombinases or other programmable nuclease systems, e.g., CRISPR/Cas, TALENs, and/or ZFNs). In some embodiments, CRISPR/Cas gene editing is used to inactivate the mouse Flt3 allele, as described elsewhere herein.

In some embodiments, a genomic modification (e.g., a deletion or an indel) is in a (at least one) region of the mouse Flt3 allele selected from coding regions, non-coding regions, and regulatory regions. In some embodiments, the genomic modification (e.g., a deletion or an indel) is a coding region of the mouse Flt3 allele. For example, the genomic modification (e.g., a deletion or an indel) may be in exon 6, exon 7, exon 8, or it may span exons 6-8 of the mouse Flt3 allele. In some embodiments, the genomic modification is a genomic deletion. For example, the mouse Flt3 allele may comprise a genomic deletion of nucleotide sequences in exon 6, exon 7, and exon 8. In some embodiments, the nucleotide sequence of SEQ ID NO: 5 has been deleted from an inactivated mouse Flt3 allele. In some embodiments, an inactivated mouse Flt3 allele comprises the nucleotide sequence of SEQ ID NO: 6.

A NSG™ Flt3$^{null}$-Tg(Hu-FLT3L) mouse provided herein, in some embodiments, expresses human FLT3L. In some embodiments, human FLT3L is expressed at a level of at least 5,000 pg/ml or at least 10,000 pg/ml. For example, human FLT3L may be expressed at a level of at least 5,000 pg/ml, 7,500 pg/ml, 10,000 pg/ml, 12,500 pg/ml, 15,000 pg/ml, 17,500 pg/ml, 20,000 pg/ml, 22,500 pg/ml, 25,000 pg/ml, 27,500 pg/ml, 30,000 pg/ml, 32,500 pg/ml, 35,000 pg/ml, 37,500 pg/ml, 40,000 pg/ml, 42,500 pg/ml, 45,000 pg/ml, 47,500 pg/ml, or 50,000 pg/ml. In some embodiments, human FLT3L is expressed at a level of 10,000 pg/ml to 30,000 pg/ml. In some embodiments, human FLT3L is expressed at a level of 15,000+/−1000 pg/mL to 17,000+/−100 pg/ml. Methods of detecting FLT3L protein expression are known and may be used as provided herein. For example, flow cytometry and/or an ELISA (enzyme-linked immunosorbent assay) using an anti-FLT3L antibody may be used to detect the level of human FLTL3 protein present in mouse tissue and/or blood.

In some embodiments, a NSG™ Flt3$^{null}$-Tg(Hu-FLT3L) mouse may also expression mouse FLTL3. In some embodiments, mouse FLT3L is expressed at a level of at least 1,000 pg/ml or at least 2,000 pg/ml. For example, mouse FLT3L may be expressed at a level of 3,000 pg/ml, 4,000 pg/ml, 5,000 pg/ml, 6,000 pg/ml, 7,000 pg/ml, 8,000 pg/ml, 9,000 pg/ml, or 10,000 pg/ml. In some embodiments, mouse FLT3L is expressed at a level of 5,000 pg/ml to 10,000 pg/ml. In some embodiments, mouse FLT3L is expressed at a level of 6,000 pg/ml to 8,000 ml.

In some embodiments, a NSG™ Flt3$^{null}$-Tg(Hu-FLT3L) mouse does not express a detectable level of mouse FLT3. A detectable level of mouse FLT3 is any level of FLT3 protein detected using a standard protein detection assay, such as flow cytometry and/or an ELISA. In some embodiments, a NSG™ Flt3$^{null}$-Tg(Hu-FLT3L) mouse expresses an undetectable level or a low level of mouse FLT3. For example, a mouse may express less than 1,000 pg/ml mouse FLT3. In some embodiments, a NSG™ Flt3$^{null}$-Tg(Hu-FLT3L) mouse expresses less than 500 pg/ml mouse FLT3 or less than 100 pg/ml mouse FLT3. The mouse FLT3 receptor is also referred to as cluster of differentiation antigen CD135. Thus, in some embodiments, a NSG™ Flt3$^{null}$-Tg(Hu-FLT3L) mouse does not comprise (there is an absence of) CD135$^+$ multipotent progenitor (MPP3) cells.

Human Innate Immune System Model

The NSG™ Flt3$^{null}$Tg(Hu-FLT3L) mouse of the present disclosure, in some embodiments, is used to support engraftment of human CD34$^+$ HSCs and development of a human innate immune system. The human immune system includes the innate immune system and the adaptive immune system. The innate immune system is responsible for recruiting immune cells to sites of infection, activation of the complement cascade, the identification and removal of foreign substances from the body by leukocytes, activation of the adaptive immune system, and acting as a physical and chemical barrier to infectious agents.

In some embodiments, the NSG™ Flt3$^{null}$Tg(Hu-FLT3L) mouse is sublethally irradiated (e.g., 100-300 cGy) to kill resident mouse HSCs, and then the irradiated mouse is engrafted with human CD34$^+$ HSCs (e.g., 50,000 to 200,000 HSCs) to initiate the development of a human innate immune system. Thus, in some embodiments, the mouse further comprises human CD34$^+$ HSCs. Human CD34$^+$ HSCs may be from any source including, but not limited to, human umbilical cord blood, mobilized peripheral blood, and bone marrow. In some embodiments, the human CD34$^+$ HSCs are from human umbilical cord blood.

The differentiation of human CD34$^+$ HSCs into divergent immune cells (e.g., T cells, B cells, dendritic cells) is a complex process in which successive developmental steps are regulated by multiple cytokines. This process can be monitored through cell surface antigens, such as cluster of differentiation (CD) antigens. CD45, for example, is expressed on the surface of HSCs, macrophages, monocytes, T cells, B cells, natural killer cells, and dendritic cells, thus can be used as a marker indicative of engraftment. On T cells, CD45 regulates T cell receptor signaling, cell growth, and cell differentiation. In some embodiments, the NSG™ Flt3$^{null}$Tg(Hu-FLT3L) mouse comprises human CD45$^+$ cells. Unexpectedly, the NSG™ Flt3$^{null}$Tg(Hu-FLT3L) mouse exhibits mucosal engraftment of human CD45$^+$ cells in the small intestines. In some embodiments, the NSG™ Flt3$^{null}$Tg(Hu-FLT3L) mouse also exhibits engraftment of human CD45$^+$ cells to tissues in the lung, thymus, spleen, and/or lymph nodes.

As CD45$^+$ cells mature, they begin to express additional biomarkers, indicative of the various developmental stages and differentiating cell types. Developing T cells, for example, also express CD3, CD4, and CD8. As another example, developing myeloid cells express CD33$^+$. The NSG™ Flt3$^{null}$Tg(Hu-FLT3L) mouse of the present disclosure, advantageously, comprises not only human CD45$^+$ cells but also double positive human CD45$^+$/CD3$^+$ T cells as well as double positive human CD45$^+$/CD33$^+$ myeloid cells.

Thus, in some embodiments, a population of human CD45$^+$ cells in a NSG™ Flt3$^{null}$Tg(Hu-FLT3L) mouse comprises human CD45$^+$/CD3$^+$ T cells. In some embodiments, the population of human CD45$^+$ cells comprises an increased percentage of human CD45$^+$/CD3$^+$ T cells, relative to a NSG™ control mouse. In some embodiments, the percentage of human CD45$^+$/CD3$^+$ T cells in the NSG™ Flt3$^{null}$Tg(Hu-FLT3L) mouse is increased by at least 25%, relative to a NSG™ control mouse. For example, the percentage of human CD45$^+$/CD3$^+$ T cells in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD45$^+$/CD3$^+$ T cells in the NSG™ Flt3$^{null}$Tg(Hu-FLT3L) mouse is increased by at least 50%, relative to a NSG™ control mouse. In some embodiments, the percentage of human CD45$^+$/CD3$^+$ T cells in the NSG™ Flt3$^{null}$Tg(Hu-FLT3L) mouse is increased by at least 100%, relative to a NSG™ control mouse. In some embodiments, the percentage of human CD45$^+$/CD3$^+$ T cells in the NSG™ Flt3$^{null}$Tg(Hu-FLT3L) mouse is increased by 25%-100%, 25%-75%, 25%-50%, 50%-100%, 50%-75%, or 75%-100%, relative to a NSG™ control mouse.

In some embodiments, a population of human CD45$^+$ cells in a NSG™ Flt3$^{null}$Tg(Hu-FLT3L) mouse comprises human CD45$^+$/CD33$^+$ T cells. In some embodiments, the population of human CD45$^+$ cells comprises an increased percentage of human CD45$^+$/CD33$^+$ T cells, relative to a NSG™ control mouse. In some embodiments, the percentage of human CD45$^+$/CD33$^+$ T cells in the NSG™ Flt3$^{null}$Tg(Hu-FLT3L) mouse is increased by at least 25%, relative to a NSG™ control mouse. For example, the percentage of human CD45$^+$/CD33$^+$ T cells in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD45$^+$/CD33$^+$ T cells in the NSG™ Flt3$^{null}$Tg(Hu-FLT3L) mouse is increased by at least 50%, relative to a NSG™ control mouse. In some embodiments, the percentage of human CD45$^+$/CD33$^+$ T cells in the NSG™ Flt3$^{null}$Tg(Hu-FLT3L) mouse is increased by at least 100%, relative to a NSG™ control mouse. In some embodiments, the percentage of human CD45$^+$/CD33$^+$ T cells in the NSG™ Flt3$^{null}$Tg(Hu-FLT3L) mouse is increased by 25%-100%, 25%-75%, 25%-50%, 50%-100%, 50%-75%, or 75%-100%, relative to a NSG™ control mouse.

The NSG™ Flt3$^{null}$Tg(Hu-FLT3L) mouse provided herein, surprisingly, is also capable of supporting engraftment of dendritic cells (e.g., plasmacytoid dendritic cells and myeloid dendritic cells), natural killer cells, and monocyte-derived macrophages (monocyte macrophages). Plasmacytoid dendritic cells (pDCs) secrete high levels of interferon alpha; myeloid dendritic cells (mDCs) secrete interleukin 12, interleukin 6, tumor necrosis factor, and chemokines; natural killer cells destroy damaged host cells, such as tumor cells and virus-infected cells; and macrophages consume substantial numbers of bacteria or other cells or microbes.

In some embodiments, a NSG™ Flt3$^{null}$Tg(Hu-FLT3L) mouse comprises an increased percentage of human CD123$^+$ plasmacytoid dendritic cells, relative to a NSG™ control mouse. In some embodiments, the percentage of human CD123$^+$ plasmacytoid dendritic cells in the NSG™ Flt3$^{null}$Tg(Hu-FLT3L) mouse is increased by at least 25%, relative to a NSG™ control mouse. For example, the percentage of human CD123$^+$ plasmacytoid dendritic cells in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD123$^+$ plasmacytoid dendritic cells in the NSG™ Flt3$^{null}$Tg(Hu-FLT3L) mouse is increased by at least 50%, relative to a NSG™ control mouse. In some embodiments, the percentage of human CD123$^+$ plasmacytoid dendritic cells in the NSG™ Flt3$^{null}$Tg(Hu-FLT3L) mouse is increased by at least 100%, relative to a NSG™ control mouse. In some embodiments, the percentage of human CD123$^+$ plasmacytoid dendritic cells in the NSG™ Flt3$^{null}$Tg(Hu-FLT3L) mouse is increased by 25%-100%, 25%-75%, 25%-50%, 50%-100%, 50%-75%, or 75%-100%, relative to a NSG™ control mouse.

In some embodiments, a NSG™ Flt3$^{null}$Tg(Hu-FLT3L) mouse comprises an increased percentage of human CD56$^+$ natural killer cells, relative to a NSG™ control mouse. In some embodiments, the percentage of human CD56$^+$ natural killer cells in the NSG™ Flt3$^{null}$Tg(Hu-FLT3L) mouse is increased by at least 25%, relative to a NSG™ control mouse. For example, the percentage of human CD56$^+$ natural killer cells in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD56$^+$ natural killer cells in the NSG™ Flt3$^{null}$Tg(Hu-FLT3L) mouse is increased by at least 50%, relative to a NSG™ control mouse. In some embodiments, the percentage of human CD56$^+$ natural killer cells in the NSG™ Flt3$^{null}$Tg(Hu-FLT3L) mouse is increased by at least 100%, relative to a NSG™ control mouse. In some embodiments, the percentage of human CD56$^+$ natural killer cells in the NSG™ Flt3$^{null}$Tg(Hu-FLT3L) mouse is increased by 25%-100%, 25%-75%, 25%-50%, 50%-100%, 50%-75%, or 75%-100%, relative to a NSG™ control mouse.

In some embodiments, a NSG™ Flt3$^{null}$Tg(Hu-FLT3L) mouse comprises an increased percentage of human CD14$^+$ monocyte macrophages, relative to a NSG™ control mouse. In some embodiments, the percentage of human CD14$^+$ monocyte macrophages in the NSG™ Flt3$^{null}$Tg(Hu-FLT3L) mouse is increased by at least 25%, relative to a NSG™ control mouse. For example, the percentage of human CD14$^+$ monocyte macrophages in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD14$^+$ monocyte macrophages in the NSG™ Flt3$^{null}$Tg(Hu-FLT3L) mouse is increased by at least 50%, relative to a NSG™ control mouse. In some embodiments, the percentage of human CD14$^+$ monocyte macrophages in the NSG™ Flt3$^{null}$Tg(Hu-FLT3L) mouse is increased by at least 100%, relative to a NSG™ control mouse. In some embodiments, the percentage of human CD14$^+$ monocyte macrophages in the NSG™ Flt3$^{null}$Tg(Hu-FLT3L) mouse is increased by 25%-

100%, 25%-75%, 25%-50%, 50%-100%, 50%-75%, or 75%-100%, relative to a NSG™ control mouse.

In some embodiments, a NSG™ Flt3$^{null}$Tg(Hu-FLT3L) mouse comprises an increased percentage of human CD11C$^+$ HLA-DR$^+$ myeloid dendritic cells, relative to a NSG™ control mouse. In some embodiments, the percentage of human CD11C$^+$ HLA-DR$^+$ myeloid dendritic cells in the NSG™ Flt3$^{null}$Tg(Hu-FLT3L) mouse is increased by at least 25%, relative to a NSG™ control mouse. For example, the percentage of human CD11C$^+$ HLA-DR$^+$ myeloid dendritic cells in the NSG™ Flt3$^{null}$Tg(Hu-FLT3L) mouse may be increased by at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, relative to a NSG™ control mouse. In some embodiments, the percentage of human CD11C$^+$ HLA-DR$^+$ myeloid dendritic cells in the NSG™ Flt3$^{null}$Tg(Hu-FLT3L) mouse is increased by at least 50%, relative to a NSG™ control mouse. In some embodiments, the percentage of human CD11C$^+$ HLA-DR$^+$ myeloid dendritic cells in the NSG™ Flt3$^{null}$Tg(Hu-FLT3L) mouse is increased by at least 100%, relative to a NSG™ control mouse. In some embodiments, the percentage of human CD11C$^+$ HLA-DR$^+$ myeloid dendritic cells in the NSG™ Flt3$^{null}$Tg(Hu-FLT3L) mouse is increased by 25%-100%, 25%-75%, 25%-50%, 50%-100%, 50%-75%, or 75%-100%, relative to a NSG™ control mouse.

Methods of Producing Transgenic Animals

Provided herein, in some aspects, are methods of producing a transgenic animal that expresses human FLT3L. A transgenic animal, herein, refers to an animal that has a foreign (exogenous) nucleic acid (e.g. transgene) inserted into (integrated into) its genome. In some embodiments, the transgenic animal is a transgenic rodent, such as a mouse or a rat. In some embodiments, the transgenic animal is a mouse. Methods of producing transgenic mice, for example, are well known. Three conventional methods used for the production of transgenic animals include DNA microinjection (Gordon and Ruddle, Science 1981: 214: 1244-124, incorporated herein by reference), embryonic stem cell-mediated gene transfer (Gossler et al., Proc. Natl. Acad. Sci. 1986; 83: 9065-9069, incorporated herein by reference) and retrovirus-mediated gene transfer (Jaenisch, Proc. Natl. Acad. Sci. 1976; 73: 1260-1264, incorporated herein by reference), any of which may be used as provided herein.

The nucleic acid encoding human FLT3L, in some embodiments, comprises a human FLT3L transgene that comprise a promoter (e.g., a constitutively active promoter) operably linked to a nucleotide sequence encoding human FLT3L. In some embodiments, the nucleic acid encoding human FLT3L used to produce a transgenic animal (e.g., mouse) is present on an vector, such as a plasmid, a bacterial artificial chromosome (BAC), or a yeast artificial chromosome (YAC), which is delivered, for example, to the pronucleus/nucleus of a fertilized embryo where the nucleic acid randomly integrates into the animal genome. In some embodiments, the nucleic acid (e.g., carried on a BAC) is delivered to a fertilized embryo of a NSG™ mouse to produce a NSG™ Tg(Hu-FLT3L) mouse. Following injection of the fertilized embryo, the fertilized embryo is transferred to a pseudopregnant female, which subsequently gives birth to offspring comprising the nucleic acid encoding human FLTL3. The presence or absence of the nucleic acid encoding human FLTL3 may be confirmed, for example, using any number of genotyping methods (e.g., sequencing and/or genomic PCR).

Also provided herein are methods of inactivating an endogenous Flt3 allele. In some embodiments, an endogenous Flt3 allele is inactivated in a transgenic animal. In some embodiments, the transgenic animal is a NSG™ Tg(Hu-FLT3L) mouse. Thus, in some embodiments, the method comprise inactivating a mouse Flt3 allele in a NSG™ Tg(Hu-FLT3L) mouse to produce a NSG™ Flt3$^{null}$Tg(Hu-FLT3L) mouse. Methods of gene (allele) inactivation are known, any of which may be used as provided herein. In some embodiments, a gene/genome editing method is used. Engineered nuclease-based gene editing systems that may be used as provided herein include, for example, clustered regularly interspaced short palindromic repeat (CRISPR) systems, zinc-finger nucleases (ZFNs), and transcription activator-like effector nucleases (TALENs). See, e.g., Carroll D Genetics. 2011; 188(4): 773-782; Joung J K et al. Nat Rev Mol Cell Biol. 2013; 14(1): 49-55; and Gaj T et al. Trends Biotechnol. 2013 July; 31(7): 397-405, each of which is incorporated by reference herein.

In some embodiments, a CRISPR system is used to inactivate an endogenous Flt3 allele, for example, to produce a NSG™ Flt3$^{null}$Tg(Hu-FLT3L) mouse. See, e.g., Harms D W et al., Curr Protoc Hum Genet. 2014; 83: 15.7.1-15.7.27; and Inui M et al., Sci Rep. 2014; 4: 5396, each of which are incorporated by reference herein). For example, Cas9 mRNA or protein and one or multiple guide RNAs (gRNAs) can be injected directly into mouse embryos to generate precise genomic edits into a Flt3 gene. Mice that develop from these embryos are genotyped or sequenced to determine if they carry the desired mutation(s), and those that do are bred to confirm germline transmission.

The CRISPR/Cas system is a naturally occurring defense mechanism in prokaryotes that has been repurposed as a RNA-guided-DNA-targeting platform for gene editing. Engineered CRISPR systems contain two main components: a guide RNA (gRNA) and a CRISPR-associated endonuclease (e.g., Cas protein). The gRNA is a short synthetic RNA composed of a scaffold sequence for nuclease-binding and a user-defined nucleotide spacer (e.g., ~15-25 nucleotides, or ~20 nucleotides) that defines the genomic target to be modified. Thus, one can change the genomic target of the Cas protein by simply changing the target sequence present in the gRNA. In some embodiments, the CRISPR-associated endonuclease is selected from Cas9, Cpf1, C2c1, and C2c3. In some embodiments, the Cas nuclease is Cas9.

A guide RNA comprises at least a spacer sequence that hybridizes to (binds to) a target nucleic acid sequence (e.g., a region of the Flt3 allele, such as the promoter sequence, a coding sequence, or a noncoding sequence), and a CRISPR repeat sequence that binds the endonuclease and guides the endonuclease to the target nucleic acid sequence. As is understood by the person of ordinary skill in the art, each gRNA is designed to include a spacer sequence complementary to its genomic target sequence (e.g., a region of the Flt3 allele). See, e.g., Jinek et al., Science, 2012; 337: 816-821 and Deltcheva et al. Nature, 2100; 471: 602-607, each of which is incorporated by reference herein. In some embodiments, a gRNA used in the methods provided herein binds to exon 6 of a mouse Flt3 allele. In some embodiments, a gRNA used in the methods provided herein binds to exon 7 of a mouse Flt3 allele. In some embodiments, a gRNA used in the methods provided herein binds to exon 8 of a mouse Flt3 allele. In some embodiments, multiple gRNAs are used to target multiple regions of the Flt3 allele. In some embodiments, two gRNAs are used, one binding to exon 6 and one binding to exon 8 of the Flt3 allele. In some embodiments, a gRNA of the present disclosure comprises the nucleotide sequence of SEQ ID NO: 1. In some embodiments, a gRNA of the present disclosure comprises the nucleotide sequence of SEQ ID NO: 2.

Methods of Use

The mouse model provided herein may be used for any number of applications. For example, the NSG™ Flt3$^{null}$-Tg(Hu-FLT3L) mouse may be used to test how a particular agent (e.g., therapeutic agent) or medical procedure (e.g., tissue transplantation) affects the human innate immune system (e.g., human innate immune cell responses).

In some embodiments, the NSG™ Flt3$^{null}$-Tg(Hu-FLT3L) mouse is used to evaluate an effect of an agent on human innate immune system development. Thus, provided herein are methods that comprise administering an agent to the NSG™ Flt3$^{null}$-Tg(Hu-FLT3L) mouse, and evaluating an effect of the agent on human innate immune system development in the mouse. Effects of an agent may be evaluated, for example, by measuring a human innate immune cell (e.g., T cell and/or dendritic cell) response (e.g., cell death, cell signaling, cell proliferation, etc.). Non-limiting examples of agents include therapeutic agents, such as anti-cancer agents and anti-inflammatory agents, and prophylactic agents, such as immunogenic compositions (e.g., vaccines).

In other embodiments, the NSG™ Flt3$^{null}$-Tg(Hu-FLT3L) mouse is used to evaluate an immunotherapeutic response to a human tumor. Thus, provided herein are methods that comprise administering an agent to a NSG™ Flt3$^{null}$-Tg(Hu-FLT3L) mouse that has a human tumor, and evaluating an effect of the agent on the human innate immune system and/or on the tumor in the mouse. Effects of an agent may be evaluated by measuring a human innate immune cell (e.g., T cell and/or dendritic cell) response and/or tumor cell response (e.g., cell death, cell signaling, cell proliferation, etc.). In some embodiments, the agent is an anti-cancer agent.

In yet other embodiments, the NSG™ Flt3$^{null}$-Tg(Hu-FLT3L) mouse is used to evaluate a human innate immune response to an infectious microorganism. Thus, provided herein are methods that comprise exposing the NSG™ Flt3$^{null}$-Tg(Hu-FLT3L) mouse to an infectious microorganism (e.g., bacteria and/or virus), and evaluating an effect of the infectious microorganism on the human innate immune response. Effects of an infectious microorganism may be evaluated by measuring a human innate immune cell (e.g., T cell and/or dendritic cell) response (e.g., cell death, cell signaling, cell proliferation, etc.). These methods may further comprise administering a drug or an anti-microbial agent (e.g., an anti-bacterial agent or an anti-viral agent) to the mouse, and evaluating an effect of the drug or anti-microbial agent on the infectious microorganism.

In still further embodiments, the NSG™ Flt3$^{null}$-Tg(Hu-FLT3L) mouse is used to evaluate a human immune response to tissue transplantation. Thus, provided herein are methods that comprise transplanting tissue (e.g., allogeneic tissue) to a NSG™ Flt3$^{null}$-Tg(Hu-FLT3L) mouse, and evaluating an effect of the transplanted tissue on the human innate immune response. Effects of a transplanted tissue may be evaluated by measuring a human innate immune cell (e.g., T cell and/or dendritic cell) response (e.g., cell death, cell signaling, cell proliferation, etc.) to the transplanted tissue.

EXAMPLES

Example 1: Production of NSG™-Tg(Hu-FLT3L) Mice

To support human DC development and innate immune function, a panel of transgenic NSG™ mouse lines expressing human FLT3 ligand (FLT3L) was produced. To produce these transgenic mouse lines, a 13.8 kilobase (kb) BamHI restriction fragment from the bacterial artificial chromosome (BAC) clone RP11-360G9 obtained from CHORI BACPAK was subcloned into pBluescript to eliminate other genes in the BAC. Purified, linearized DNA was then injected into the pronuclei of NOD.Cg-Prkdc$^{scid}$ Il2rg$^{tm1Wjl}$/SzJ (NSG™) fertilized eggs.

Eleven founders were identified by PCR. Of these founders, four founder lines (lines 3, 7, 8, and 10) had detectable levels of circulating human FLT3L when tested by enzyme linked immunosorbent assay (ELISA). These founders were mated with NSG non-transgenic mice. The transgenic offspring of this cross were tested by ELISA for circulating human FLT3L levels. The levels of FLT3L in transgenic NSG mice that were hemizygous or homozygous for the human FLT3L transgene (lines 7 and 8) ranged from 400 to 600 pg/mL (FIG. 1).

Example 2: NSG™-Tg(Hu-FLT3L) Mice Exhibit Impaired Development of Human HSCs

Figure 2:
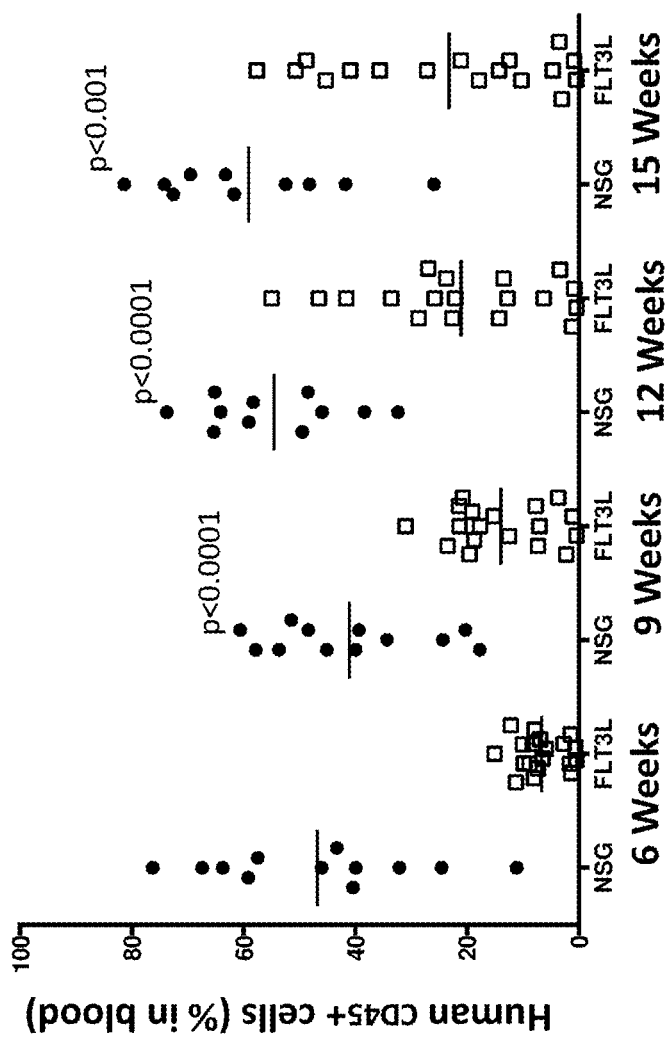
FIG. 2 shows decreased levels of human hematopoietic stem cell (HSC) engraftment in homozygous NSG™-Tg (Hu-FLT3L) mice that are expressed as percentages of human CD45+ cells in blood. Each data point represents the percentage of human CD45+ cells in individual mice tested at 6-15 weeks post-engraftment. Both male and female mice were used.

Transgenic NSG™ mice expressing human FLT3L (NSG™-Tg(Hu-FLT3L)) were then engrafted with human cord blood CD34$^+$ HSCs. Cohorts of NSG™-Tg(Hu-FLT3L) mice and NSG™ non-transgenic control mice were sublethally irradiated (200 cGy) and injected intravenously with 100,000 human umbilical cord blood HSCs. Flow cytometry of peripheral blood from engrafted mice was conducted at 6, 9, 12, and 15 weeks post-engraftment. Unexpectedly, the percentage of human CD45$^+$ cells was significantly lower in the NSG™-Tg(Hu-FLT3L) mice compared with NSG™ controls at all time points tested (FIG. 2).

Example 3: Production of NSG™ Flt3$^{null}$Tg(Hu-FLT3L) Mice

To test whether the decreased human HSC engraftment in NSG™-Tg(Hu-FLT3L) mice is a consequence of human FLT3L activating the host mouse DCs and possibly other innate immune mouse components, the gene encoding the mouse FLT3 receptor (Flt3) was knocked out (to prevent human FLT3L from binding to the mouse FLT3 receptor and activating mouse innate immunity). Without being bound by theory, without the mouse FLT3 receptor, both the human FLT3L and mouse FLT3L would be available to bind to the human FLT3 receptor.

The mouse Flt3 gene encoding the FLT3 receptor was knocked out directly in the NSG™-Tg(Hu-FLT3L) homozygous strain that expressed the human FLT3 ligand. To knock-out the mouse Flt3 gene, two single guide RNA (sgRNAs, see Table 1 below) were designed to target exons 6 and 8, which should eliminate the immunoglobulin-like domain, even if the transcript is retained and a hypomorph results. The sgRNAs were designed using breaking Cas (6) and Zifit (7) software to minimize the likelihood of off-target cutting and were also checked against the human sequence to ensure the human FLT3L transgene would not be targeted. Both sgRNAs were designed as Tru-Guides ("truncated"), each with only 19 base recognition sites, in order to further reduce the likelihood of off-target cutting (8). The sgRNAs were prepared as described previously (9).

The screening for mouse Flt3 knock-outs was performed using PCR primers (see Table 1 below) that flanked the region of interest (e.g., exons 6-8). The PCR primers yield a 1942 base pair (bp) wild-type amplicon, with a predicted size of 670 bp for the mutant dropout ("DO") allele. Following PCR, samples were screened by Sanger sequencing using the same primers. Three founders carrying knock-out alleles were identified by PCR and subsequently sequenced. Three knock-out lines were established (Lines 1, 2, and 4) by intercrossing N2 mice from the founder with the largest deletion. Knock-outs were typed by PCR, and ultimately, a single knock-out line was expanded, validated, and characterized (NPD.Cg-Flt3$^{em1Mvw}$Prkdc$^{scid}$Il2rg$^{tm1Wjl}$Tg(Hu-FLT3L)7Sz, abbreviated as NSG™ Flt3$^{null}$Tg(Hu-FLT3L) mice.

Figure 3:
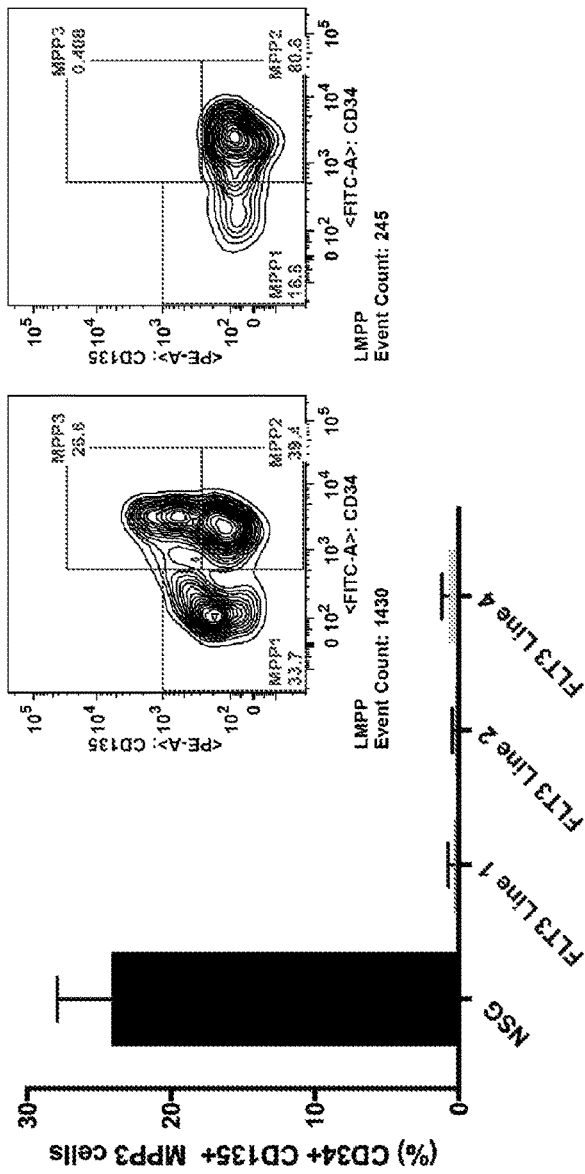
FIG. 3 shows the absence of mouse CD135+ myeloid multipotential (MMP3) progenitor cells in NSG™ Flt3$^{null}$-Tg(Hu-FLT3L) mouse bone marrow. Each bar represents values from three (3) female mice at ten (10) weeks of age.

The modified Flt3$^{null}$ allele lost 1500 bp beginning before exon 6 and termination just before the end of exon 8. The deleted gene sequence is shown as SEQ ID NO: 5 (1500 base pairs deleted in the mouse Flt3 receptor gene in NSG™ Flt3$^{null}$-Tg(Hu-FLT3L) mice). The resulting PCR product for the modified Flt3$^{null}$ allele is 442 bp. The sequence of this PCR product is shown as SEQ ID NO: 6 (PCR product resulting from targeted mouse Flt3 gene deletion). Mouse FLT3 receptor is called cluster of differentiation antigen CD135. The NSG™ Flt3$^{null}$ Tg(Hu-FLT3L) mice were validated for lack of mouse FLT3 by flow cytometry of bone marrow dendritic cells by absence of CD135$^+$ multipotent progenitor (MPP3) cells (FIG. 3).

TABLE 1

Sequences used to generate and screen Flt3 knock-out mice

| Sequence | Name | SEQ ID NO: |
|---|---|---|
| 5'-GAACAGCUUGGUGCAUUCG | sgRNA-Exon 6 | 1 |
| 5'-GAUGGUCACCAACGCUGAC | sgRNA-Exon 8 | 2 |
| 5'-CCAACCTGAACTGTATGGAGATAG | PCR-Forward | 3 |
| 5'-CCACAGGGAAAGCCACTAAA | PCR-Reverse | 4 |

Figures 4A, 4B:
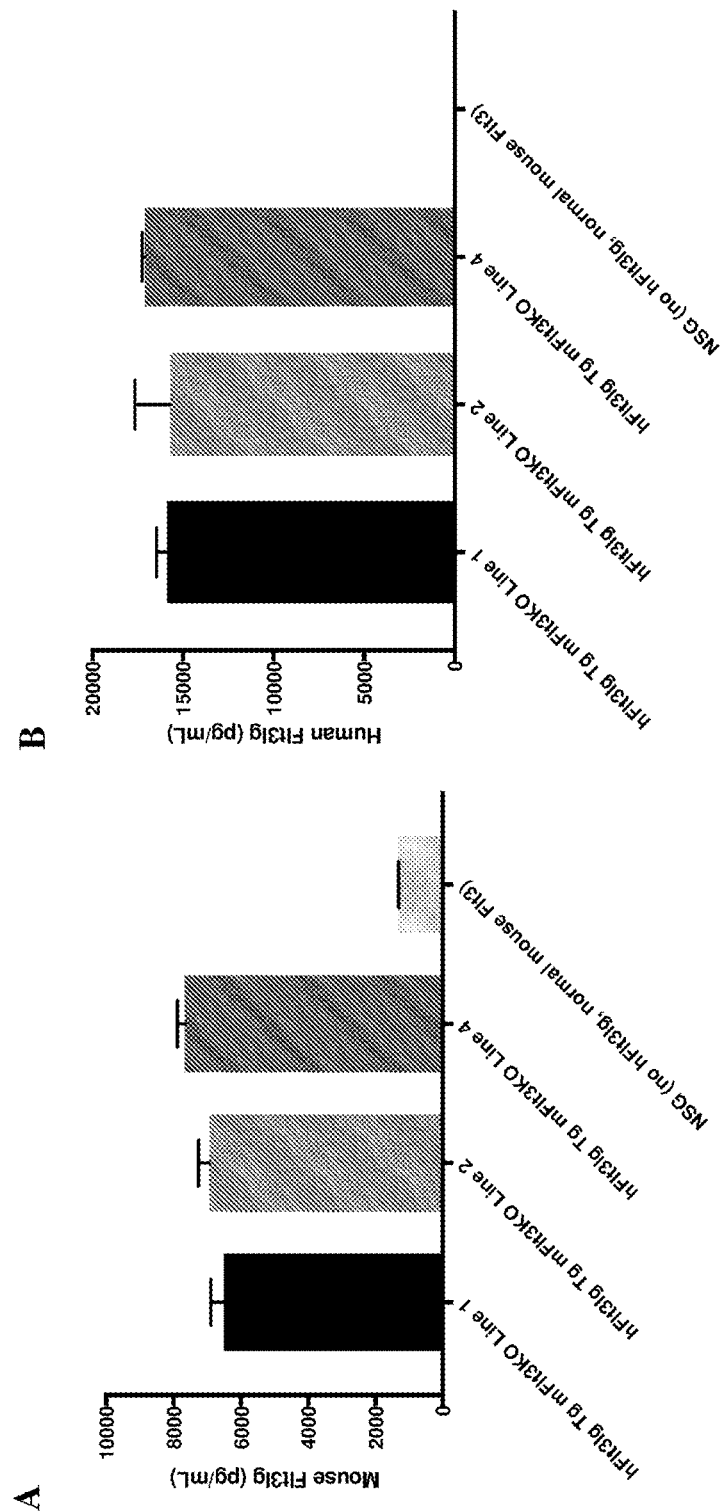
FIG. 4A shows the levels of mouse FLT3L in NSG™Flt3$^{null}$-Tg(Hu-FLT3L) and NSG™ control mice.
FIG. 4B shows the levels of human FLT3L in NSG™ Flt3$^{null}$-Tg(Hu-FLT3L) and NSG™ control mice.
Figures 5A, 5B, 5C, 5D:
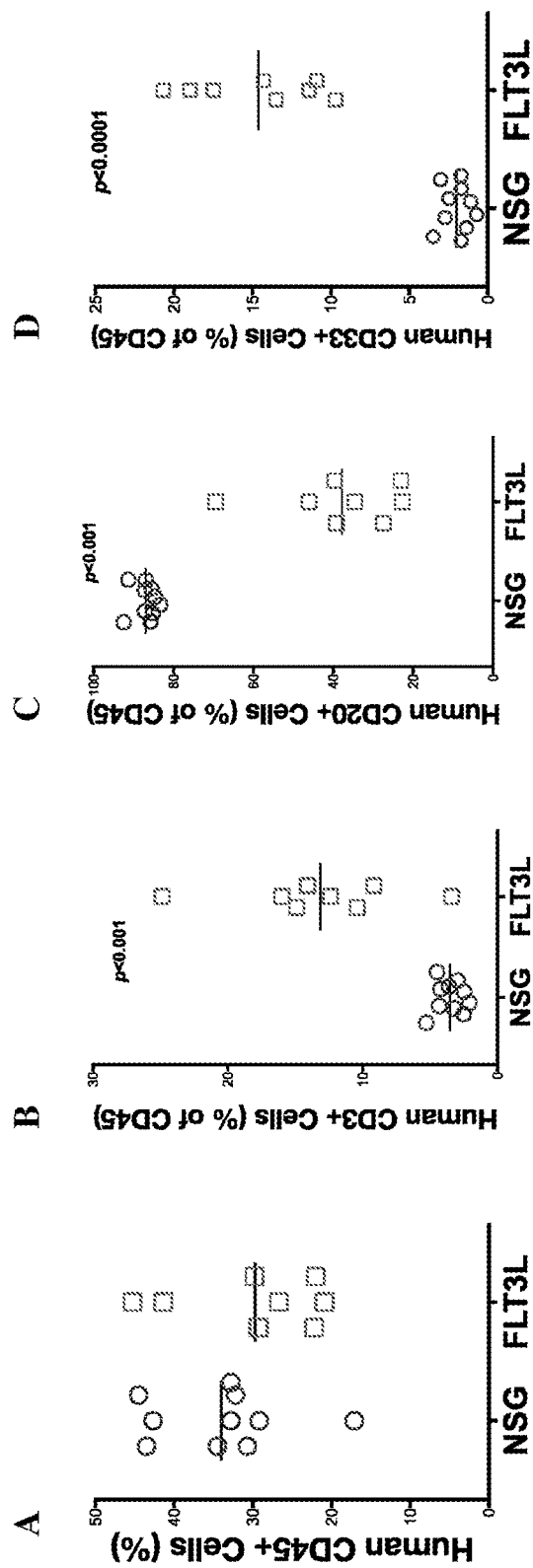
FIG. 5A shows human CD45+ T-cell development in NSG™ Flt3$^{null}$-Tg(Hu-FLT3L) mice engrafted with human HSC and CD45+ T-cell development in NSG™ control mice. Eight (8) NSG™ Flt3$^{null}$-Tg(Hu-FLT3L) mice and ten (10) NSG™ control mice were injected at 8-12 weeks of age. Both male and female mice were used.
FIG. 5B shows an increased percentage of human CD3+ T cell development in NSG™ Flt3$^{null}$-Tg(Hu-FLT3L) mice engrafted with human HSC compared with NSG™ control mice.
FIG. 5C shows a decreased percentage of human CD20+ B-cell development in NSG™ Flt3$^{null}$-Tg(Hu-FLT3L) mice engrafted with human HSC compared with NSG™ control mice. This may be due to an increase in the percentage of HSCs differentiating into innate immune system cells (e.g., dendritic cells, natural killer cells, monocytes, macrophages, eosinophils, basophils, neutrophils) as opposed to adaptive immune system cells (e.g., T cells and B cells).
FIG. 5D shows increased percentage of human CD33+ myeloid cell development in NSG™ Flt3$^{null}$-Tg(Hu-FLT3L) mice engrafted with human HSC compared with NSG™ control mice.
Figures 6A, 6B, 6C, 6D:
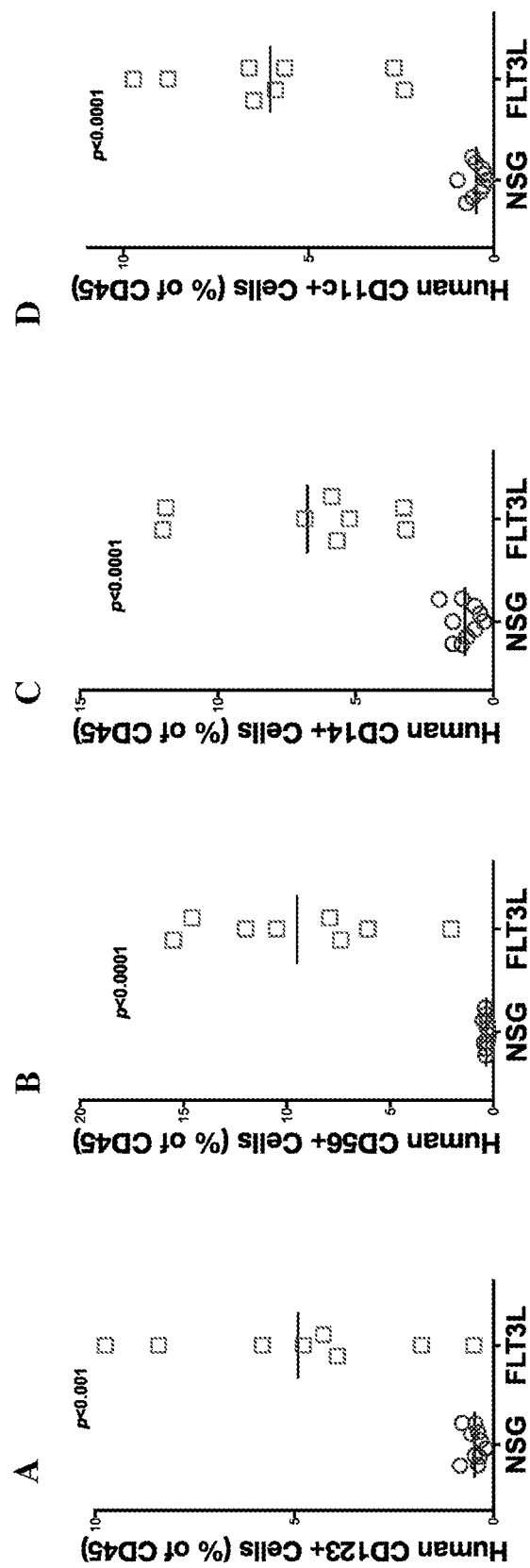
FIG. 6A shows increased human CD123+ plasmacytoid dendritic cell (DC) development in NSG™ Flt3$^{null}$-Tg(Hu- FLT3L) mice engrafted with human HSC compared with NSG™ control mice. Eight (8) NSG™ Flt3$^{null}$-Tg(Hu-FLT3L) mice and ten (10) NSG™ control mice were injected at 8-12 weeks of age. Both male and female mice were used.
FIG. 6B shows increased human CD56+ natural killer cell (NK) development in NSG™ Flt3$^{null}$-Tg(Hu-FLT3L) mice engrafted with human HSC compared with NSG™ control mice.
FIG. 6C shows increased human CD14+ monocyte/macrophage cell development in NSG™ Flt3$^{null}$-Tg(Hu-FLT3L) mice engrafted with human HSC compared with NSG™ control mice.
FIG. 6D shows increased human CD11c/HLA-DR+ myeloid DC cell development in NSG™ Flt3$^{null}$-Tg(Hu-FLT3L) mice engrafted with human HSC compared with NSG™ control mice.

Example 4: NSG™ Flt3$^{null}$Tg(Hu-FLT3L) Mice Support Dendritic Cell Development ELISA assays of the sera of the NSG™ Flt3$^{null}$ Tg(Hu-FLT3L) mice expressing the human FLT3L transgene and lacking the mouse FLT3 receptor showed levels of the human FLT3L ranging from 15,175+/−1,137 pg/mL to 17,120+/−92.7 pg/mL. Sera from the NSG™ non-transgenic control mice showed no detectable FLT3L levels (FIGS. 4A-4B). The levels of mouse FLT3L ranged from 6,000 to 8,000 pg/mL in NSG™ Flt3$^{null}$Tg(Hu-FLT3L), while the level of mouse FLT3L in NSG™ control was ~ 1,000 pg/mL.

To determine the ability of the NSG™ Flt3$^{null}$ Tg(Hu-FLT3L) mice to support engraftment with human CD34+ HSC and development of a human immune system, groups of NSG™ Flt3$^{null}$ Tg(Hu-FLT3L) mice (n=8) and NSG™ control mice (n=10) at 8-12 weeks of age were sublethally irradiated (200 cGy) and injected intravenously (IV) with 100,000 human umbilical cord blood CD34+ HSC. Flow cytometry analyses of the peripheral blood of the engrafted mice at 6, 9, 12, 15, and 18 weeks post-engraftment showed that the NSG™ Flt3$^{null}$Tg(Hu-FLT3L) and NSG™ control mice had similar percentages of human CD45+ leukocytes. However, in the human CD45+ cell population, the NSG™ Flt3$^{null}$ Tg(Hu-FLT3L) mice had significantly increased percentages of both human CD3+ T cells and human CD33+ myeloid cells (FIGS. 5A-5D and FIGS. 8A-8C).

Figure 7:
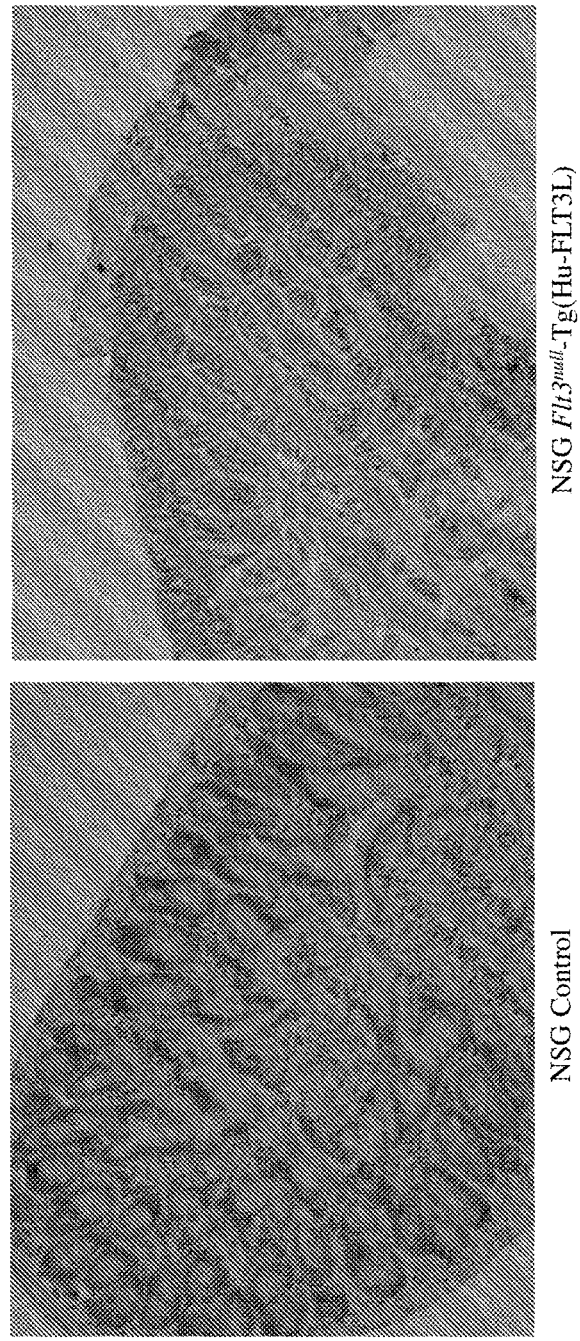
FIG. 7 shows the small intestine from a NSG™ Flt3$^{null}$-Tg(Hu-FLT3L) mouse and a NSG™ control mouse showing mucosal engraftment with HSC. Eight (8) NSG™ Flt3$^{null}$-Tg(Hu-FLT3L) mice and ten (10) NSG™ control mice were injected at 8-12 weeks of age. Both male and female mice were used.
Figure 8A:
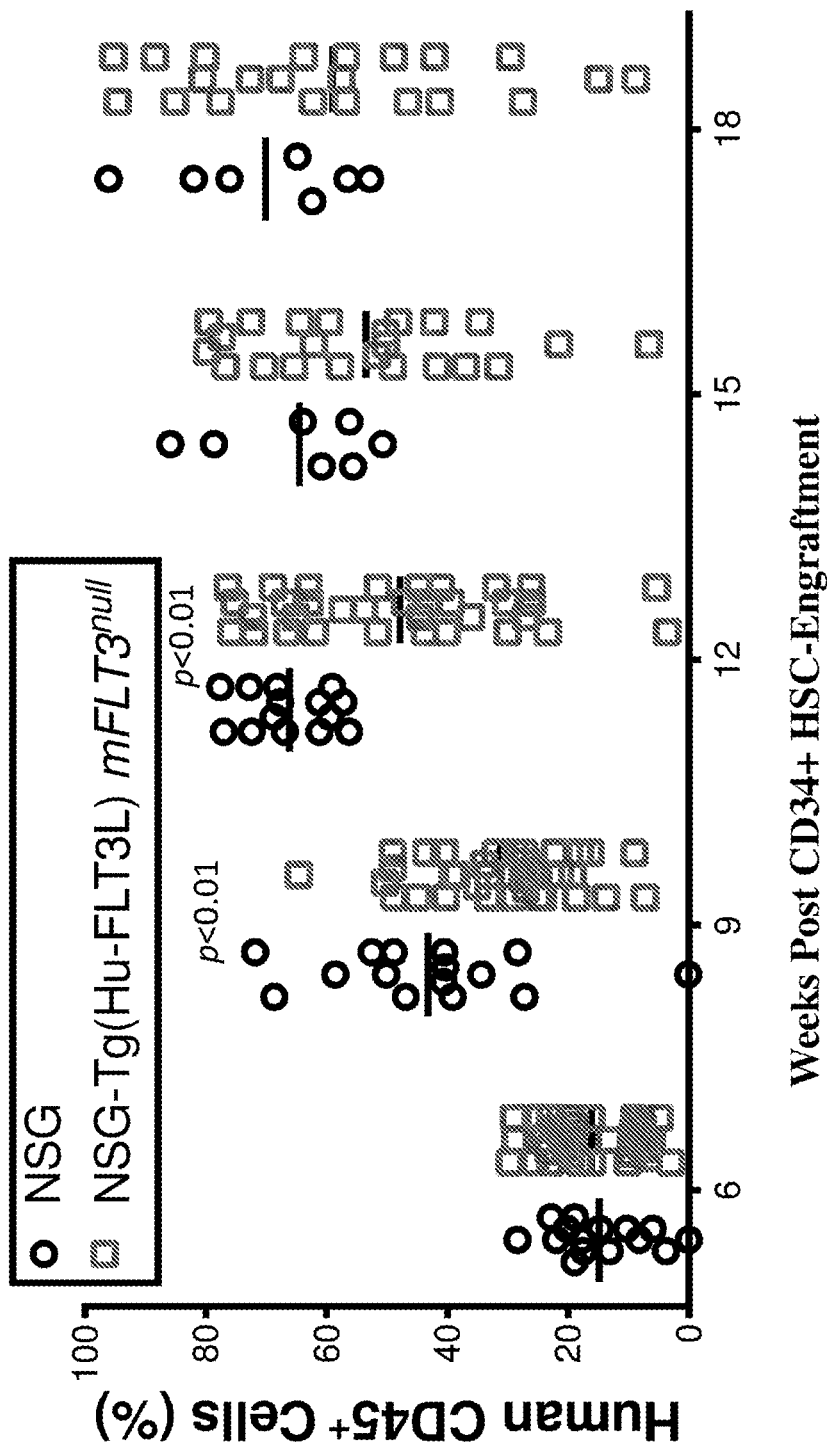
FIG. 8A shows comparable human CD45+ cell development in NSG™ Flt3$^{null}$-Tg(Hu-FLT3L) mice engrafted with human HSC compared with NSG™ control mice.
Figure 8B:
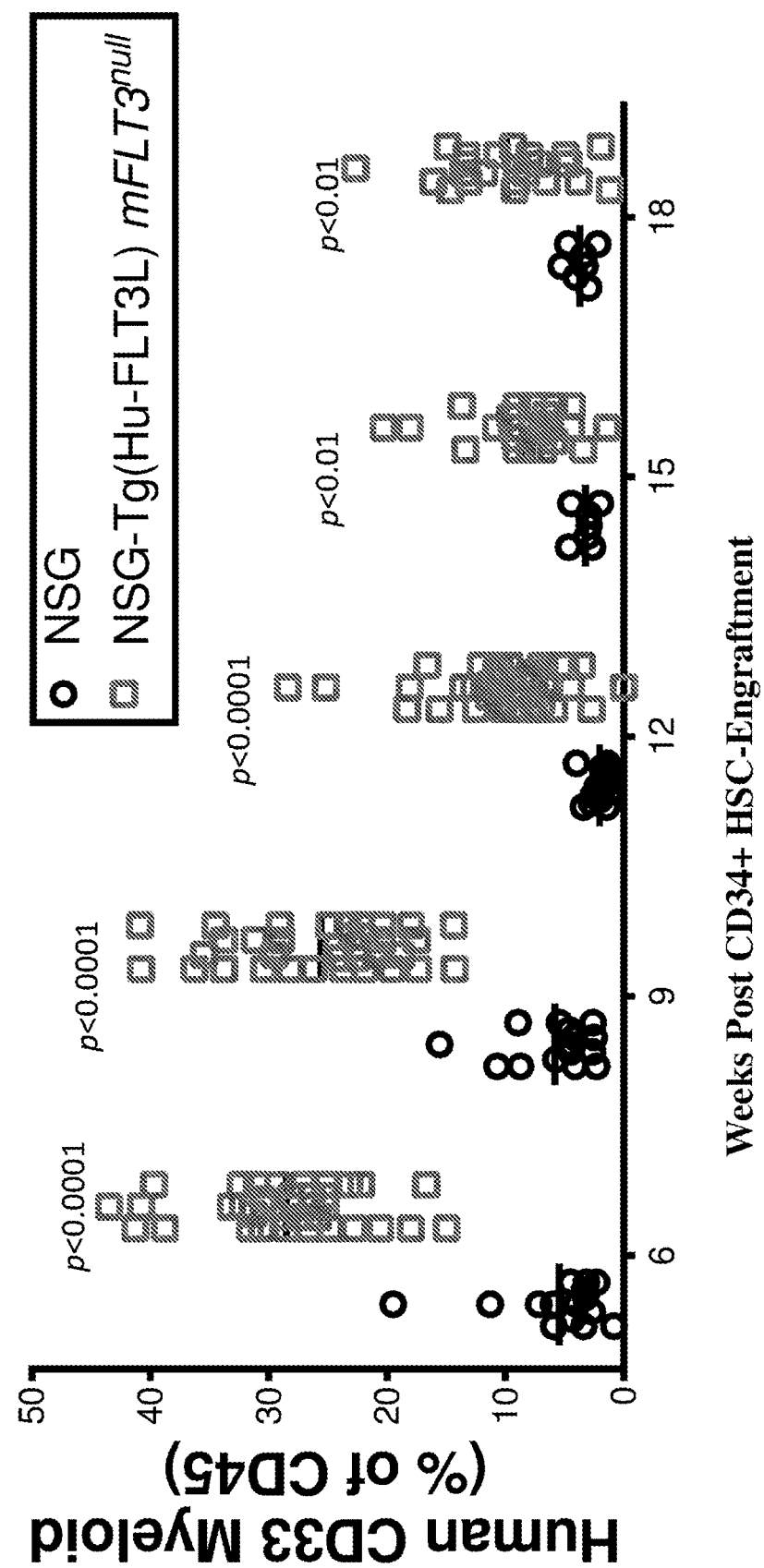
FIG. 8B shows increased human CD33' myeloid cell development in NSG™ Flt3$^{null}$-Tg(Hu-FLT3L) mice engrafted with human HSC compared with NSG™ control mice.
Figure 8C:
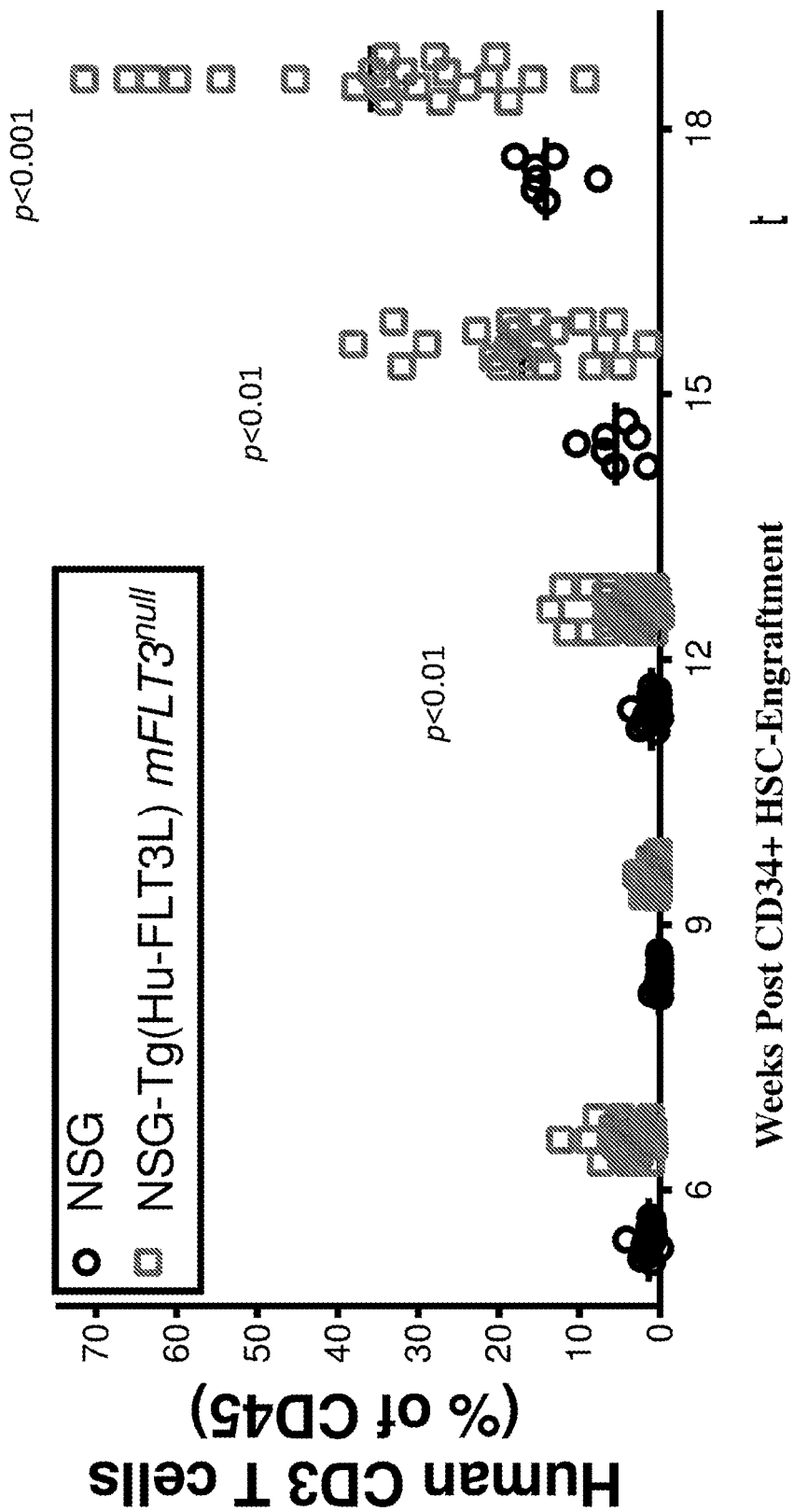
FIG. 8C shows increased human CD3+ T cell development in NSG™ Flt3$^{null}$-Tg(Hu-FLT3L) mice engrafted with human HSC compared with NSG™ control mice.
Figure 8D:
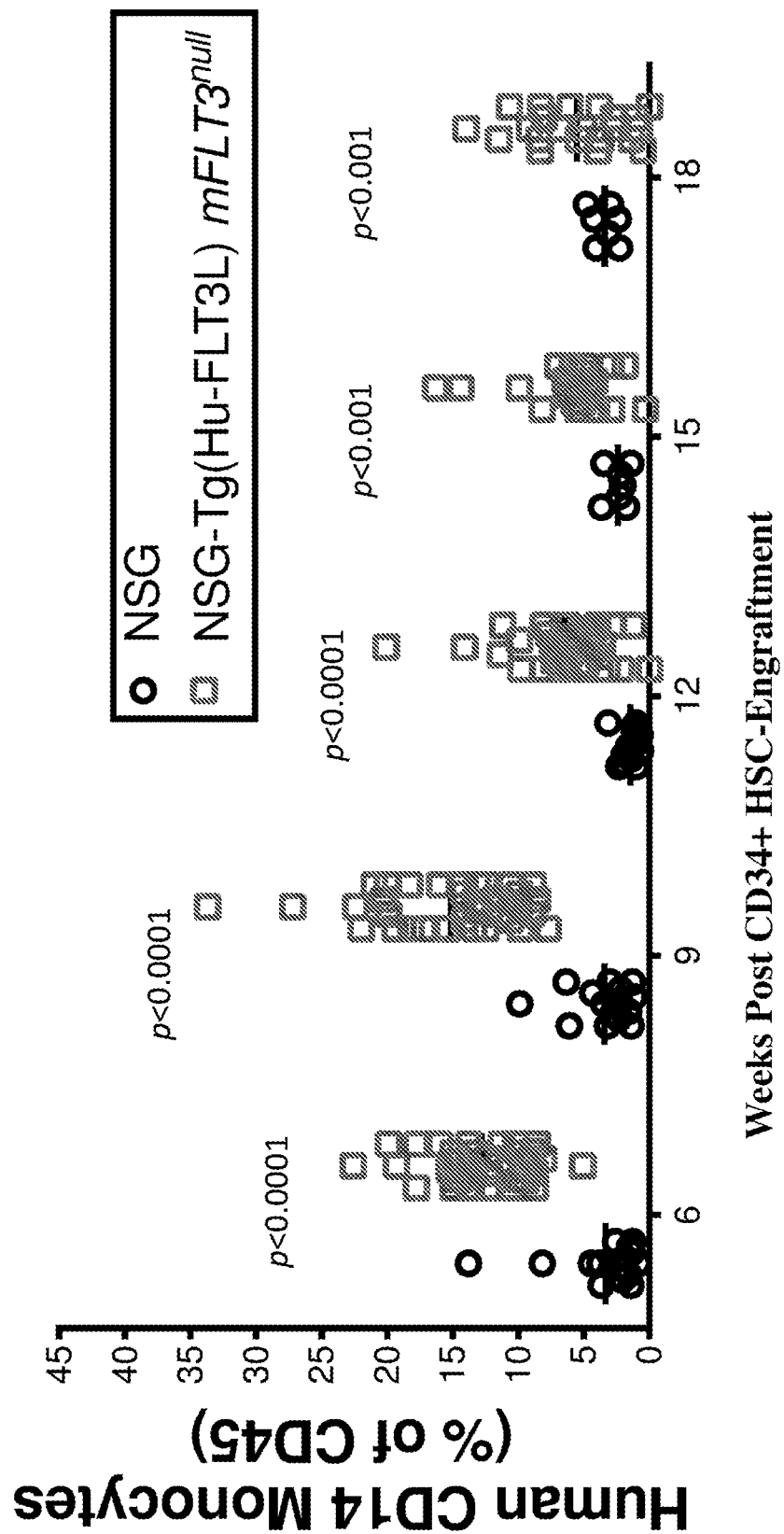
FIG. 8D shows increased human CD14+ monocyte cell development in NSG™ Flt3$^{null}$-Tg(Hu-FLT3L) mice engrafted with human HSC compared with NSG™ control mice.
Figure 8E:
FIG. 8E shows increased human CD11c+ HLA-DR+ myeloid dendritic cell development in NSG™ Flt3$^{null}$-Tg(Hu-FLT3L) mice engrafted with human HSC compared with NSG™ control mice.
Figure 8F:
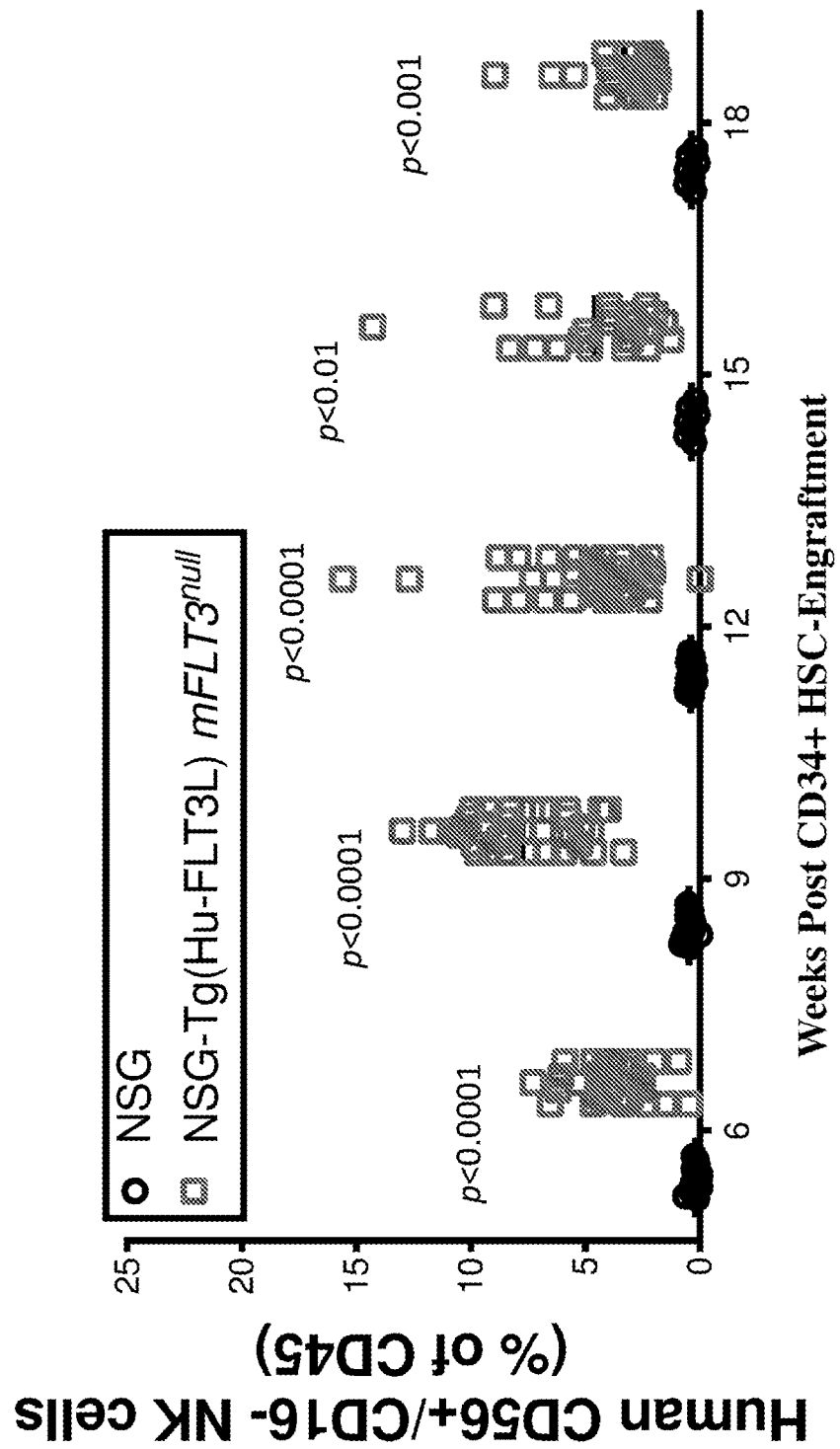
FIG. 8F shows increased human CD56+ natural killer (NK) cell development in NSG™ Flt3$^{null}$Tg(Hu-FLT3L) mice engrafted with human HSC compared with NSG™ control mice.

NSG™ Flt3$^{null}$ Tg(Hu-FLT3L) mice also showed increased percentages of human CD123+ plasmacytoid dendritic cells, CD56+ human natural killer (NK) cells, CD14+ human monocyte macrophages, and CD11C+ HLA-DR+ human myeloid dendritic cells (FIGS. 6A-6D, 8D-8F). Moreover, histochemical analyses of tissues from the engrafted mice unexpectedly showed mucosal engraftment of human CD45+ cells in the small intestines of NSG™ Flt3$^{null}$Tg(Hu-FLT3L) mice (FIG. 7).

SEQUENCES

```
ATCCCCCAGTGCTGGTGACCTTGAACACAGGGTCTGCCCTGAGCAGTGCTGACAGCCTGTTAGCTGTCATTTTGAAG
CATTTCCTGAAGGAAACTTACCTTATCATTGCAGCTGTAAAGAAGAAGGCCCTGCTGTTGTCAGAAAGGAGGAAAAG
GTACTTCATGAGTTGTTCGGAACAGACATCAGATGCTGTGCTAGAAATGCACTGGGCCGCGAATGCACCAAGCTGTT
CACCATAGGTAATGGGGGACTGTCGGCTATGTGTCCTTAGTGACGGTTCCTAAGGGACCGGTGATAGCTTCTGTGTG
GGTAATCATTCCACTTCAGAAAGATGATGGAAAGTTATACTGAAATCCGAATCTAGATCGAATAGTCCACATTCTGA
CATAAAAGCAATTGAACACACAGGTATGGCCAAGCTTGGTGGCCCGGGCTTTTAATCCTTCTTTCATAGGACTTTGA
TTTGATTCAATTTGATTTGATTTGATTTGACTTAGGTGCTGGGCTCAAACCCAGGGACTCAGAGCATCTGCTTTGCC
ACTGAGTTCCACTCCAGATCTTTTGCACCACTTTATTTATTTATTTATTGTGTGTGTGTATACACACATTAAATACA
CACACATACACACACACACACACACACACACACACACACACACACACACACGCTACAGCATGTAATGTGGA
TGTCAGGTTCTCTTCTTGTCATATGGGCCCCTGGATCAAATTCAGGTCAGTCTGGCAGCGGCAGGCACCTCCACCC
ACTGAGCCATCTTGATGCCCCGTTCATACCATTTACAATGTAACACTGTAGATTCTGTAAGGGAGGATTTCTGCAAC
AAAGGGTATTCCATCTCGAGTGGGTGGTTTTACTCTGTCGCTTTTTTTTTTTAGTTTTGTGCTGCTCTGTGACTCC
AGGTCTTCTCCAGGCCAGCCTCTTTTACCCTGATCTTCTCAGCTCTGCATTGTTTGGCTTGATTAGTGATGGCAGGG
ATGCTGACACCATTGCTTTTCAAAACGTTTGCGACACTTCTGAGCTGAGGCAAAAGTTTTTAAAAAAAAGATGTGCT
TTTTTTTTTTTTTTTTGTCTTCTTTGGGATATTTTTATCTTCTAGATCTAAACCAGGCTCCTCAGAGCACACTGCC
CCAGTTATTCCTGAAAGTGGGGGAACCCTTGTGGATCAGGTGTAAGGCCATCCATGTGAACCATGGATTCGGGCTCA
```

| SEQUENCES |
|---|
| CCTGGGAGCTGGAAGACAAAGCCCTGGAGGAGGTAACAGCGCCCACCCGTGGTGTTTACCGTAAGCTCTCAGCGTGG |
| GCTGGAAACCCGGAATACAGACTCCCCTTTCATTAATACTCAGGGCAGCTACTTTGAGATGAGTACCTACTCCACAA |
| ACAGGACCATGATTCGGATTCTCTTGGCCTTTGTGTCTTCCGTGGGAAGGAACGACACCGGATATTACACCTGCTCT |
| TCCTCAAAGCACCCCAGCCAGTCAGCGTTGGTGACCA (SEQ ID NO: 5) |
| CCAACCTGAACTGTATGGAGATAGCTTGTCTATGGGAAAAAAAATCACCAAATAAAATAAAATCTAAAATATTAAA |
| TAATAAAGTAATACTGTAACATTATCCTAATTAGATACAGAGTAGCTAGCTGGTCCCTGCAGATTCCAGGCTGGATA |
| CAGTTGAGTTAATTTTTCATCTGCTCTTTTCTTCCATCCCTAAAAATATACTTTGTAACTTCATCCCCTAAACATAC |
| TGGGTCCCCCCACCCCATCCTAGGTAACGGGCTCACGAAATTTGGGGTTGGTTGGTTTGTTTGTTTTTAATGCTGTC |
| CTGGAACTCGCTGTGTAGATTGGTTGGCCTTGAACTCACAGAAATCTACCAGCATCTGCCTCCCCAGTGCTGGGATT |
| AAAGGCACAGGCCACCAAGCTTGACTCTGCTTGTGTCTTTAGTGGCTTTCCCTGTGG (SEQ ID NO: 6) |
| GATCCCTGTGCTCCTCCGAGTGGCACAGGAAACTTGGCTGATAGAGGCGCTCTCTCCATGCATCCTCCACCATCCAC |
| TCCCCGGTCCCTTAGACTTCCATTCAGAAGTGACACCTGTCACCTCCACCCTCATGTGACTGGCCAAAGTGAGTGTG |
| GCCATGTCCGAGTTCCCCAGGATGGGACCTCGAATCCTCCTGCTGGGGGGTGGGGCAGCAGATGTTTCAGGACAG |
| TCTGCCACGGATCAGATGGGTGAGCAAGAGATTCAGGATGGGCGTGATGGGTCACACCTGTAATCCCAGCATTTTGG |
| GAGGCCGAGGCAGGCTGATCACCTGAGGTCAGGAGTTCGAGATCAGCCTGGCCAACATAGTGAAACCTCGTCTCTAC |
| TAAAAATACAAAAATTAGCCGGGCATGGTGGCACGCACCTGCAATTCCAGCTACTTGGGAGCCTGAGGCACAAGAAT |
| TGCTTAAGCCCAGGAGGCGGAGGTTGCCGTGAGCCGAGACTGTGCCACTGCACTCCAGCCTGGGCAACAGAGTGAGA |
| CCCCATCTAAAAAAAAAAAATGCTTCAGAGATTCAGAGATCCACAGATGTGGAAGAGAGCTTCTATTTTGTCTCATG |
| TACCACCTCACCCCTCAGTTTGGAGTTGGAGAAGCCGAGGCTTAGAGAGGTCAAGGGGCTGGCCAAGCTCCCACAGT |
| GATAAAGCTAGTGCTAGGGCGACACCTGCCAGGCCCAATGTGACAAGATGCATCCTGAGTCCTGTGTGCCAAGCCTT |
| GGCGGGGCAAAGTTGGGGCCCGGAGGACGGTAAGACACAGCAACTGCGAGTTCCCAGAGACAGATCCGGGTTCCAGC |
| CCCAGCTCACCATGCACTGGGCGTGCCACCCAGGGAGTCAGCCCCACTGCAGCCCCGCTGCGGGGCGTCCGGAGAA |
| CGCGCCATCTGCGGCGTGAGCGGCCGCCTCTCACCACCAGGGGGCGCGCTCCGCCTGGGCCCAGATTCCACCCCTTG |
| ACTGTCTCCCCCCAAAAATTTCCTTTCACTTTCGGTCTCTGGCTGTCACCCGGCTTGGCCCCTTCCACACCCAACTG |
| GGGCAAGCCTGGTGCGTGAGGAGACTTGGACTCTAGGTCCCCAAGGGGCGGAGCCAGGGTCCCCACTCCTGGGGCAG |
| GGGGAGCAGAGGGTGGGGGGCTGGGTTCCCGGGTCCCTAACCTGGGGAGGGTTCTGGGGACCAGACGTCGAGGTTCT |
| TAGAAGTGGAGATGAAGAGTTTTCACCGTAACTGGGGCAGACGCAGGAAGCCTGGGGGAGGAAGGGGCGGAAACTCA |
| GCCACATCAATGGGACGCGGGAGGGGCGGGAGGCAAAGGGGCGGGCAGGGCAGGGCTGGGCATGAGGGTCCGAG |
| ACTTGTTCTTCTGTCCCTTCCAAGACCCGGCGACAGGAGGCATGAGGGGCCCCGGCCGAAATGACAGTGCTGGCGC |
| CAGCCTGGAGCCCAACAGTGCGTAAACCCCAGGGACAAGATCAGGGGAGAGGGGAGGCACAATGTCAGGATGGGCA |
| GAGATGAGGGGAGATGGACGGGAGAACAGATGGACAGATGACGAGGAAATAGGAGGGGAGATGGACAGATGTGAGGG |
| GAGATGGATAGGAGAGGAGACGGACAGAGGAGGGGGAGATGGACAGAGGATGGGGAGATGGACAGAGGAGGGGAGA |
| TAGAGGAGGGGAGATAGAGAGGAGTGGGAGATGGACAGGAGCGGGGAGATGGACAGAGGAGGGGGAGATGGACAGA |
| GGAGAGGGCAGATGAACAGAGGAGAGGGAGATAAAGAGGAGGGAGGTGGACAGGAGGAGGGAGATGGACAGAGAAGG |
| GGGAGATGGACAGAGGTGGGGGAGATGGACAGGAGGGAAGATGGAGAGGAGGGGTATGGACAGAGGAGAGGGAGA |
| TGGACAGGAGGGGAGATGGACAGAGGAGAGGGAGATGAAGAGGAGGGGAGGTGGACAGGAGGAGGGAGACGGACA |
| GAGGAGAGGAAGAGAGACAGAGGAGGGGGAGATGGACAGAGGAGGGGAGATGGACAGAAAAGGGGGAGATGGAC |
| AGAGGAGAGGGAAGGTGGACAGAGCCAAGAACAAATGAAGAGGACGTGGACCAAGATCAAGAGAGAAGCAGGCAACA |

| SEQUENCES |
| --- |
| GTGGTGTAGAAGGCAGAGGGAGGGACAGAGCTGGAGGAACCCGGGCGAGGAAACCAGACGTGAAGATGAGGTGGTTG |
| GAGAGAGACCAGCAGAGTGGGGGAGATGGGGAGAGAGAGGGGTGGGGCAGAGGGGGATGCAAACTGGACAGCATTGG |
| ACCAGAGGCAGAGAGAAACCGGGAAAGACAGGCAGAGATGGGGCCATGTCTCCAGAAAGTGTGGAAGAGGCAGAAGG |
| ACACCCAGGGAAGGAGGAGCGGGGAAGACAGAACAGTACAGGTGGGAAGCCCGGAGGAGGGGCTGTGTGTGGAACA |
| GCAGAGGGCTCCCCCAGCACCCGCTCCCCTGCAGACCTATCTCCTCCTGCTGCTGCTGCTGAGCTCGGGACTCAGTG |
| GGACCCAGGACTGCTCCTTCCAACACAGCCCCATCTCCTCCGACTTCGCTGTCAAAATCCGTGAGCTGGTGAGCGGC |
| GCTGCCCCGGACCCCCTCATGTGATCCCCCTTCCCCCCACTTTTTTTTTTAAGTAGAGATGGGGTCTCTCTCCCTGT |
| GTTTCCCAGGGTGGTCTTGAACTCCTGGGCTCAAGCGATCCTCCCACCTTGGCCTCCCAAAGTGCTGGAATTACAGG |
| CGTGAGCCACTGTGCTTAGGGGTGTCATCCCTTTTTAAGGGCAAGGTTCTGTGGCTTCTTCTGGGCTCCCCCTCTCT |
| TGGTCTTGTCCCTCTCTCTGGATCTCTGCTGCCACCTCTGGGTCCCCACAGTTCTGTTTCTCGCTGTTTTCAGCC |
| AGGCCTGATCCTGTTTTCTCCCGCAGTCTGACTACCTGCTTCAAGATTACCCAGTCACCGTGGCCTCCAACCTGCAG |
| GACGTAAGTCATGTTGGGAGGGACCTGGGATGGAGGTGGGGACCACAGACTCAAGATGCTCCACCGAGGCGAGTGGA |
| TAACCAGGCCCTCCCCTCCCCAAACCCAGGAATCAGAGTCCTCAGCCCCTCCTCCCTCAGACCCAGGAGCCCCGGCC |
| CAGCCCCTCCTCCCTCAGACCCAGCAGCCCCGTGCCCAGCTCCTCCCTCAGACCCGTGGGTTCTCCCCTCTAGGAGG |
| AGCTCTGCGGGGGCCTCTGGCGGCTGGTCCTGGCACAGCGCTGGATGGAGCGGCTCAAGACTGTCGCTGGGTCCAAG |
| ATGCAAGGCTTGCTGGAGCGCGTGAACACGGAGATACACTTTGTCACCAAATGTGCCTTTCAGGTCAGCCCTCAACT |
| TAGGGGACAAGTGAGGGGAGGGAGATGCCTTCCTACGAATTAGAAGTAAAGCTCCACTAGGCCTTATTGGCGATTTG |
| GACCATAGCCACCCAACGAAGGTAGAGCGAGAAGCGCCACCCTGCAGAGCCCTGTTCCTACAGAACAACACGTCCCC |
| AGGCACCGGTGATGGGGAGCAGTCTGGTCCCATTCTGGGGCCCCGGTTTCCTAGGCCATGATGAAGGGTGCCACTGA |
| GGGGTTCTTCCCCAAAAAAAAACAGGGAGAGAAGGGGTCTCTAAACTGAGGAGGCCGGGCGTGGTGGCTCACTCCT |
| GTAATCCTAGCACTTTGGGAGGCTGAGGTGGGCGGATCACTTGAGGTCAGGAGTTTGAGACCAGCCTGGCCAACATG |
| ATGAAATCCCGGCTGTACTAAAAATACAAAAATTAGCCGGGCATGGTGGCTCAGGAGGCTGAGGCACAGGAATCGCT |
| TGAACCCGGGAGCCAGAGGCTGCAGTGAGCCGAGATCATGCCACTGCACTCCAGCCTGGGAGACAGAGTGAAACTGT |
| CTCAAAAACAAAACAAACAAACAAAAACCTCTCTCTGAGGGCTGGGTGCAGTGGCTCACACCTGTAATCCCAGCACT |
| TTCGGAGGCCAAGGTGGGAGGATTATTTGAGCCCAGGAGTTCAAGACCAGCCCGGGTAACACAGTGAAACCTCATCT |
| CTGCACAAAAATAAAAATAAATTAGCCAGGCATGGTGGTGCCCACCTGTGGTCCCAGCTACTCAGAAGGCTGAGGTG |
| GGAGGATCACTTGAGCCCTGGAGGTCGAGGCTGCGATGAGCTATGATTGGGCCACTGCACTCCAGCTTGAGCGACAG |
| AGCAAGACCCTGTCTCAAAACATAGAATAGGCCGTGTATGGTGGCTCACGACTGTAATCCCAGCACTTTGGGAGGCT |
| GAGGCGGGTGGATTGCCTGAGCTCAGGAGTTCGAGACCAGCCTCGGCAACGTGATGAAAACCATCTCTACTAAAATA |
| CAAAAACAAAATTAGCCAGGCATGGTGGTGGGCACCTGTAGTCCCAGCTACTTGGGAGACTGAGGCAGGAGAATTGC |
| TTGAACCCAGGAGGCAGAGGTTGCAGTGAGCCGAGATCACACCACTGCCCTCCAGCCTGGGCGACAGAGCAAGACTC |
| CATCTCCAAAAAAATAAAAATAAATAAAAGCCTGGGTACAGTGGCTCACGCCTGTAATCCCAGCACTTTGGGAGCC |
| CGAGGCGGGCAGATCACGAGGTCAGGAGTTTGAGACCACCCTGGCCAATGTGGTGAAACCCCGTCTCTACTAAAAAT |
| ACAAAAATTAGCTGGGCATGGTGGCGCGCGCCTGTAGTCCCAGCTACTCAGGAGGCTGAGGCAGAATTCCTTGAACC |
| CGGGAGGTAGAAGTTGCAGTAAGCCGAGATCGTGCCACTGTACTCCAGCCAGGGTGACAGAGCAAGACTCTGTCCCC |
| AAAAAATAAATAAATAATAAAGTAACTTTGGGAGGCCGAGGCGGGCGAGTCACCTGAGGTCAGGAGTTCGAGACCAG |
| CCTGGCCAACATAGAGAAACCCCGTTTCTACTAAAAAATATAAATAAATAAATAAATAAATAGGCTGGGCACG |
| GTGGCTCACGCCTGTAATCCCACACTTTGGGAGGCCGAGGCGGGCGGATCACAAGGTCAGGAGATCAAGACCATCCT |
| GGCTAACACAATGAAACCCCATCTCTACTAAAAATACAAACAATTAGCCGGGCGTGGTGGCAGGCGCCTGTAGTCCC |

-continued

| SEQUENCES |
|---|
| AACTACCTGGGAGGCTGAGGCAGGTGAATGGCGTGAAACCAGGAGGCGGAGCTTGCAGTGAGCCGAGATTGCGCCAC |
| TGTACTCCAGCCTGGGCAACAGAGCGAGACTCTGTCTTAAAAATAAATAAATAAATATGGCCAAGCACGGTGG |
| CTCATGCCTACAATCCCAGCACTTTGGGAGGCCAAGGTGGGCAGATCACCTGAGGTCAGGAGTTCGAGACCAGCCTG |
| GCCAACATGGAGAAACCCCGTCTCTACTACAAATACAAAAAATAGCTGGGCATGGTGGTGGGCACCTATAGTCCCAA |
| CCACTGAGGAGGCTGAGGCAGGAGAATCACTTGAACCTGGGAGGCAGAGGTTGCATTTCACCACTCCAGCCTGGGCA |
| ACAGAGTGAGACTCTATCTCAAAAAAAAATTAATTAATTAAATAAATAAACTCTGAGAGCCAGAGCTCACTGGGCCC |
| TGTTGCTGGGCATCGCCAGCAGGGAAGGGCCTTTGGCCTGCGGAGGGGCGGTGGGGGATGACGTGGTGGTGACGTC |
| TCCCTCCCTGCTCCCAGCCCCCCCCAGCTGTCTTCGCTTCGTCCAGACCAACATCTCCCGCCTCCTGCAGGAGAC |
| CTCCGAGCAGCTGGTGGCGCTGAAGCCCTGGATCACTCGCCAGAACTTCTCCCGGTGCCTGGAGCTGCAGTGTCAGC |
| CCGGTAAAGGCTTCCAGGCACCCCCACTCCTTCCCCTCCTGTCCTCACGGCCGCTCCTCCTCTCTGCACAGTGCATC |
| CCAGACCCCATCTTTCTCATATTGGTTGTGACAAGGGCAAGCTTATTCCTCTTTCTGGAGCTCAGTTTACCAATTTT |
| TTTTTTTTTTTTTGAGACGGAGTCTCGCACTGTCGCCCAGGCTGGAGTGCAGTGGCGTGATCTTGGCTCACTGCAA |
| GCTCCGCCTCTCGGGTTCATGCCATTCTCCTGCCTCAGCCTCCCAAGTAGCTGGGACCACAGGCGCCCGCCACCACA |
| CCCGGCTAATTTTTTGTATTTTTAGTAGAGACGGGGTTTTACCGAGTTAAACCAGGATGGTCTCGATCTCCTGACCT |
| TGTGATCCACCTGCCTTGGCCTCCCAAAGTGCTGGGATTACAGGCGTGAGCCACAGTGCCCAGCCTACCTTTTTTTT |
| TTTTTTTTTTTGAGATGGAGTCTTGCTCTGTCCCCAGGCTGGAGTGCAGGGGTGCTATCTCGGCTCACTGCAAG |
| CTCTGCCTCCTGGGTTCACGCCATTCTCTTGCCTCAGCCTCCCCAGCAGCTGGGACTACAGGCGCCTGCCACCTCAC |
| GCGGCTAATTTTTTTTTTGTATTTTTAGTAGAGACGGTGTTTCACCGTGTCAGCCAGGATGGTCTCGATCTCCTGA |
| CCTCGTGATCTGCCCGCCTCGGCCTCCCAAAGTGCTAGGATTACAGATGTGAGCCACCGCGCCCAGCCTATTGTTTT |
| TTTTTTCTAAGTCGGAGTCTTGCTCTGTCGCCCAGGCTGGAGTGCAGTGGCGCAATCTTGGCTCACTGCAACCTCCA |
| TCTCCAGGGTTCAAGCGAATCTTCTGCCTCAGCCTTCCGAGTACCTGGGATTACAGATGCGCATACCATGCCTGGCT |
| AGTTTTTGTGTTTTAGTAGAGATGGGTTTTCACCATGTTGGCCAGGCTGGTCTTGAACTCCTGACCTCAAGTGATC |
| CACCCACCTTGGCCTCCCAAAGTGCTGGGATTATAGGCGTGAGCCACCGCGCTCAGCCTATTCACTCATTTAATTTG |
| TGACAGTCTGATGAGGTAGGTACAATGATTATCCTAGTTTTACAGATGAGCAAACTGAGGCACAGAGAGGCCAAGCA |
| GCCCATCCAAGGTCACACAGCCAGTGGCAGCCAGGCCTCTCTTTCCTTCCTTACCCCAGCCCTTCTCCTTGGTCACC |
| CAGCCTCCTCTTTCTCCCCAGACTCCTCAACCCTGCCACCCCCATGGAGTCCCCGGCCCCTGGAGGCCACAGCCCCG |
| ACAGCCCCGCAGCCCCCTCTGCTCCTCCTACTGCTGCTGCCCGTGGGCCTCCTGCTGCTGGCCGCTGCCTGGTGCCT |
| GCACTGGCAGAGGACGCGGCGGAGGACACCCCGCCCTGGGGAGCAGGTGAGCAGGCTGGGAAGAGGGGGTGAGGGGG |
| CCGAGAGGGTGGCCCACTTGTGGCTGACACTTTGGGGCCCACAGGTGCCCCCGTCCCCAGTCCCCAGGACCTGCTG |
| CTTGTGGAGCACTGACCTGGCCAAGGCCTCATCCTGGTGAGTCCTTCCTGGGCTATGGGCCTGGACTTTGTGTCTG |
| CAGGTTGGGAGGGTCACTAGGAGGCCATGGAAGGGTGGTGAGCAGTGGAGGGCAGGGCAGCTCTAGGTGCAGAAA |
| GACCCCTCTGGGGCCAGGCGCGGTGGCTCACGCCTGTAATCCCAGCACTTTGGGAGGCCGAGGCGGGTGGATCACTT |
| GAGGTCAGGAGTTCAAGACCAGCCTGGCCAACATGGCAAACCCCAGTCTCTACTAAAAATACAAAAATTAACTGGGC |
| ATAGTGGTGTGTGCCTGTAATCCCAGCTACTCAGGAGGCTGAGGAAGGAGAATTGCTTGAACCCAGGAGGCGGAGGT |
| TGCAGTGAGCCGAGATTGCGCCACTGGACTCCAGCCTGAGTGACAGAGCTAGACTCCGTCTCAAAAAAAAAAAAAAA |
| AAAGAAAAGGAAAGACCCCTCTGGGGCCACGGAGACAGACTGGAGACCAAGCCGGAGGCTGTGGGAAGGCCCAGGGT |
| GAGGACCATGACTGAGCCAGGGCTGGGACCATGGGATGGAGTGGAGTGGATGGGCAGAGAGTCAGGGGTCAGAGATC |
| AGGAGGGACCGGCCTGGGGCCTGACAGGCTTGAGTTGGCACAGATAGCCCTGGTCCAGTGATGGGGTGGACAGGGGG |

| SEQUENCES |
|---|
| GAACCTGGGGGAGGAGTCAGATTAGGGAAAGACATGGAGCTCACTGGGGACCTGAAGGAGCAAGGGGCCCTGGGGAG |
| ATCTGTGGATGTGGGAGTTTGCAAGCCTCCTGGGACAGGAAGGAAATGGCATTCCAGAAAGAGGGAACTGCCTTTGG |
| AAGCCCTTTGGTATGAGAAAGCTCAGGGTGTTCCAGTAACTTGGGCCAGCGTGGGGCAGCAAGGAGCCATGGGAGGT |
| GTGAGAGGGAGGAAAGGAGCTGGGAACAGGTGTGGAGGGTGCAGGCAGGTAGGCAGGTGGGCCAGGAGGGAAGAAGG |
| AGGGGAGGCCCCAGCGGGTCCCCTAACATTTCAAATCTAACATTTTGTAGTAATTGCTCGCACATATAGTGCCTTGG |
| TAATGCAGGCCTCATGTGGGGCTGGCTTGCTTGCTTTATTTTTTTTGAGATGGACTCTCACTCTGTCACCCAGGCT |
| GGAGTGCAGTGGCGGGATCTTGGCTCACTGCAACCTCCACCTCCCAGGTTCAAGCAATTCTCCTGCCTCAGCCTCCC |
| AAGTAGCTGGGATTACAGGCGCCCGCCACCATGCCTGGCTAATTTTTTGTATTTTTAGTAGAGATGGGGTTTCGCCA |
| TGTTGGCCAGGCTGGTCTCAAACTCCTGATCTCAGCTGATCCGCCCGCCTCAGCCTCCCAAAGTGCTGGGATGACAG |
| GTGTGAGCCACTGTTCCTGGCCCATGCTGGGCTTTCCACAAATGAACTCACTTCCTTGAGAAGTTCGTGCCATTATG |
| ATCCCAAGGCATAGAGAGGTAAATAATTTGCCAAAAGTCACACAGCTCAAGGGTGACAACCAAGATTTGACTTCAGG |
| TTGTCTTTTTTTTTTTTGAGATGGAGTCTTGCTCTGTCGCCCAGGCTGTAGTGCAGTGGCATGATCTCGGCTCAC |
| TGCAGCCCCGCCTCCCAGGTTCAAGTGATTCTCCTGCCTCAGCCTCTGGAGTAGCTGGGATTACAGGTACCCACCA |
| CCACACTCGGCTAATTTTTGTATTTGTAGTAGAGACGGGGTTTCACCATGTTGGCCAGGCTGGTCTCGAACTCCTGA |
| CCTTAGCTGATCCGCCCGCCTCAGCCTCCCAAAGTGCTGGGATTACAGGCATGAGCCACCGCCCGGCCTCGAGTT |
| TGTCTTGATCCAGCATCTGTGCCCTTCACTCTGCTGCCTCAGTTTCCTGATCTGTACAAAAGGCTCTAATAATAGTC |
| CTTCCACCATAGGGTTGTTATGGGGTGAAGTGAAGTGACACAGGCAAGGCTCTTAGAGCAACGCAGTGGAAACGGCA |
| TGTGAGCCACCTGTGCGATTTTCACTTTCCTGGTAGCCACATTTTTTTTTTTTTCCTGAGATGGAGTCTCACTC |
| TGTCGCCAGGTTGAAGTGCAGTGGTGTGATCTCAGCTCACTGCAACCTCCACCTCCCGGGTTCAAGCGATTCTCCTG |
| CTTCAGTCTACCGAGTAGCTGGGATTACAGGCACGCGCCATCACGCCCGGCTAATTTTTGTGTTTTTAGTAGAGAC |
| AAGGTTTCACCATGTTGGTCAGGCTGGTCTCGAACTCCTGACCTCATGATCCACCCGCCTCAGCCTCCCAAAGTGCT |
| GGGATTACAGGCGTGAGCCACCGCGCCCGGGGTCACAGTTTTTAAAAAAGGAAAAAGAAGCAGGTAACTTTATTTTA |
| TGCAGTATATCCAAAATGTTGTTATTTCAACATGTAATCAGTATTTCTCAATGATTAATGAGACATTAATCAGTTGG |
| AATCATTCATCATTTTGGGATATTTTACATTCTTTTGTCATACTAAGCCTTCAGCATCCAACGTATAGTTTATTTAT |
| TTATTTATTTTTCCTTTTGAGATGGATTCTCGCTCTGTCACCCAGGCTGGAGTGCAGTGGCGCGATCTCAGCTCACT |
| GCAACCTCGGACTCCCTGGTTCAGGCGATTCTCCTGCCTCAGCCTCCCGAGTACCTGGGATTACGCCACCACACCCA |
| GCTAATTTTTGTACTTTTAGTAGAGACCGGGTTTCACCATGTTGGCCAGGATGATCTCCATCCCCTGACCTCGTGAT |
| CCGCCCGCCTCAGCCTCCCAAAGTGCTGGATTACAAGTGTAAGCCACCGCGCCCAGCCCAGACAATAAATTTTTATC |
| AGAAATGCTTCATCTATATTTAAATTTCATGAAATTTACAGTTGCCAAAAGTAGACTCACATAGTCAAGTTGTTCAA |
| AACATACATTAAACCAGCCTGGGCCACATGGTGAAACCCCATCTCTACAAAAAATTTTAAAAAGTAGCTGGGTGTGG |
| TGGCACATGCCTGCAGTCCCAGCTACTTAGGAGGCAAAGTAGGAGGATTGCTTGAGCCCAGGAGGTCGAGGCTGCAG |
| TGAGCCCTGATTGTGCCACTGCACTCCAGCCTGGGTGAGAGAGCAAGACCCTGTCTCAAAAACAAAAAAACCACACA |
| GAAGAGTTTAGAATCCCAGTTGCTATCTCTGGGAATCATCATGATTGCTAAGACCGGTATCTATCCAACAACAACAA |
| AAATAATTAGTGCACTCCAGCCTGGGCAATAGAGGGAGACTCTGTCTCAAAAAAAAAAAAAAAAAAAAAAAAGAT |
| CAAAGACCAGTATCTAAATTGCTCTGTCGCCCAGGGTGGAGTGCAGTGGCACGATCTCGGCTCACTGCAACCTCCGC |
| CTCCCGGGTTCAAGTGATTCTCCTGCCTCAGCCTCCCCAGTAGCTTGGACTACAGGCGCGTGCCACCACACCCAGCT |
| AATTTTTGTATTTTTAGTAGAGGTAGGGTTTCACTATGTTTGCCAGGATTGTCTCGATCTCTTGACCTCGTGATCTG |
| CCCGCCTCAGCCTCCCAAAGTGCTGGGATTATAGGCGTGAGCCACCACGCCCAGCCTATCTTTTTTTTTTTTTAA |
| GAAAAGGTAATACATTGAGCAGTTTTCCTCCCAACCTAGTCCCTGTCCAATCTGTTTCCTGTCTTAAATTTATTTTT |

-continued

| SEQUENCES |
|---|
| TATTATAATTTTTTTTTTTTTTTTTTGTGAGACAGACTTTTGCTCTTGTTAGCCAGGCTGGAGTGCAGTGGTGC |
| TATCTTGACTCACGGCAACCTCCACCTCCCAGGTTCAAGCGATTCTCCTGCCTCAGCCTCTGGAGTAGCTTGGATTA |
| CAAGCGCCTGCCACCACGCCCAACTAATTTAGTGTATTTTTAGTAGAGACGGGGTTTCTTTTGTTGTTGTTGTT |
| TTTGAGACGGAGTCTCACTCTATTGCCCAGGCTGGAGTGCAACGGCACGATCTCGGCTCACTGCAACATCTGCCTCC |
| CGGGTTCAAGCGATTCTACTGCCTCAGCCTCCTGAGTAGCTGGGATTACAGGCACACACCACCACACCTGGCTAATT |
| TTTGTATTTTTAGTAGAGATGGGGTTTCACCATATTGGCCAGGCTGATCTCGAACTCCTGACCTCGTGATCTGCCCG |
| CCTTGACCTCCCAAAGTGATAGGATTACAGCCATGAGCCGCCCTGCCCAACTAATACCTGATATTAATTTTATTGTA |
| TCTCACCCAGCATGGTGGCTCACACCTGTAACTCCTTGGCAGATCGCTTGAGCCTAAGAGTTCAAGACCAGCTTGGG |
| CAACATGGTGAAACCCCGTCTCTACTAAAAATATAAAAATGAGCTGGGCATGGTGGCGTGCACCCGTAATCCCAGCT |
| AACTCAGGAGGCTGAGGCAGGAAGAATGGCTTGAACCCGGGAGGCAGAGGCTGCAGTGAGCTGAGATCATGCCACTG |
| CATTCCAGCCTGAAACAGAGCAAGACTGTCTCAAAAGAAGTTTAAGTCCAGCCTCAAACTCCTGGACTCAAGTGATC |
| CTCCTGCCTCAGCCTCCTGAGTAGTGCACCGGCCCCATCTCAAGTGTTCAGTATTCACATGTGGCTTGTTACTCCCG |
| TATTAAAGAGCAAAAATAGAGAACGTTTCTTTTTCTTTTTTTCTTTTTTTTTTTTTTTTGAGATGGGAGTTTCGC |
| TCTTGTCGCCCAGGCTGGAGTGCAATGGCACGATCTTGGCTCACCGCAACCTCTGCCTCCCAGGTTCAAGCGATTCT |
| CCTGCCTCAGCCTCCCAAGTAGCTGGGATTACAGACATGCACCACCATGCCTAGCAAATTTTGTTTTTGTTTTTGTT |
| TTTTTCTTTTGAGACAGACTTTTGCTTTTATTGCCAAGGCTGGAGTGCAATGGTGCAATCTCGACTCACTGCAACCT |
| CCGCCTCCCGGGTTCAAGCAATTCTCCTGCCTCAGCTAATTTTGTAGTTTTAGTAGAAACGGTTTCTCCATGTTAGC |
| TAGGCTGGTCTCAAACTCCCAACCTCAGGTGATCCGCCCGCCTCGACCTCCTAAAGTGCTGGAATTACAGGCGTGAG |
| CCACTGTGCCTGGCCCTAATTTTGTATTTTTAGTAGAGATGGGGTTTCTCCCTGTTGGTCAGGCTGGTCTCAAACTC |
| CCAACCTAAGGTGATCCACCAGCCTCAGCCTCCCAAACTGCTGGGATTATAGGCATGAGCCACCGCGCCCGGGGAAA |
| TATAGGGAACATTTCTATCATGGCCACGTTCTCTTGGACAGCAATGCCCTAGCACATAGTAAGCGCTTGCTGGGAAT |
| GGAGTTGTTTTGGGCATAAATCTGTGGCCCGCCCCAAGCTAAGCTACTTTCCCTCTCCTCTCTCAGCGGAGCCTTAA |
| ACAACGCAGTGAGACAGACATCTATCATCCCATTTTACAGGGGAGGATACTGAGGCACACAGAGGGGAGTCACCAGC |
| CAGAGGATGCATAGCCTGGACACAGAGGAAGTTGGCTAGAGGCCGGTCCCTTCCTTGGGCCCCTCTCATTCCCTCCC |
| CAGAATGGAGGCAACGCCAGAATCCAGCACCGGCCCCATTTACCCAACTCTGTACAAAGCCCTTGTCCCCATGAAAT |
| TGTATATAAATCATCCTTTTCTACCAGCTCTGGCCAGGTCTGTCTATGGATGGGTGTGAATGGGGTAGTTTTGATTT |
| CAGAATCTTGGTTTTTGAATTGCAATGCAATGTTTCATTCAATACGTGTTTTCTGAGGTCCCCTGGAGCCCCGGGCC |
| GGCGCTGGGCAATGTCAGAGCCTGGATTTGAGTCAGAACCAGCCCAGGTGCCCCAGGTCTCCTTGGCTATGGACGAG |
| AAGACAAGGGATTCAGCGAGCCTGGGTGCAGGATGCCATAGGCTACTATGGAGATAAAACAGAGGCAGTGTGAGGGG |
| CAACTCACCCAGGCAGGGAGAGCAGAGAGGCTTTCCAGAGCCAAATGGCATTGCGATGGTGACAAGCCAGATTTGGA |
| GGGGGTGGGAGGGCATCCTGGGCAAGGGACCCAGCTGAAGCAAAGGCCGACAGTCCAGAAAGTGAGAAGTTCCTCT |
| GAGGAACGCTCAGTGGATTGGTGCAGCCAGGCAACTAGAAGCCATTCCTTGATCCACTCTTAGAGCCCCTGGGGAAG |
| ACCACCTCCATCTGTTTTACAGATGGATAAACTGAGGCCCAGATAAGGCCAAGGGTTTCTCCAGGTCACAGTGAAGT |
| CGACCAGACACAGGAATCCAAATCTCTAAGCCTAGAATGGGCAAGGCTCCGGGGCTCACGCCGGTAATCCCAGCACT |
| TTGGGAGGCCGAAACGGGAGGATCGCTTGAGCCCAGGAGTTCGAGATCAGCCTGGCCAACATGTCAGACTCCCCCCG |
| TTCCCGGGCCACAACAAAATATATATATATATATATATTAGCCAGGCATGGTGGCGCGCCCCTGTAGTCCAAGTTAC |
| TCGAGAGGCTGAGGCAGGAG (SEQ ID NO: 7) |

REFERENCES

1. P. Tsapogas, C. J. Mooney, G. Brown, A. Rolink, The Cytokine Flt3-Ligand in Normal and Malignant Hematopoiesis. *International journal of molecular sciences* 18, (2017).
2. C. J. Mooney, A. Cunningham, P. Tsapogas, K. M. Toellner, G. Brown, Selective Expression of Flt3 within the Mouse Hematopoietic Stem Cell Compartment. *International journal of molecular sciences* 18, 60 (2017).
3. L. D. Shultz, M. A. Brehm, J. V. Garcia-Martinez, D. L. Greiner, Humanized mice for immune system investigation: progress, promise and challenges. *Nat Rev Immunol* 12, 786-798 (2012).
4. K. Palucka, J. Banchereau, Cancer immunotherapy via dendritic cells. *Nature reviews. Cancer* 12, 265-277 (2012).
5. J. S. Do, B. Min, IL-15 produced and trans-presented by DCs underlies homeostatic competition between CD8 and {gamma}{delta} T cells in vivo. *Blood* 113, 6361-6371 (2009).
6. J. C. Oliveros et al., Breaking-Cas-interactive design of guide RNAs for CRISPR-Cas experiments for ENSEMBL genomes. *Nucleic acids research* 44, W267-271 (2016).
7. P. D. Hsu et al., DNA targeting specificity of RNA-guided Cas9 nucleases. *Nature biotechnology* 31, 827-832 (2013).
8. Y. Fu, J. D. Sander, D. Reyon, V. M. Cascio, J. K. Joung, Improving CRISPR-Cas nuclease specificity using truncated guide RNAs. *Nature biotechnology* 32, 279-284 (2014).
9. B. E. Low, P. M. Kutny, M. V. Wiles, Simple, Efficient CRISPR-Cas9-Mediated Gene Editing in Mice: Strategies and Methods. *Methods Mol Biol* 1438, 19-53 (2016).

All references, patents and patent applications disclosed herein are incorporated by reference with respect to the subject matter for which each is cited, which in some cases may encompass the entirety of the document.

The indefinite articles "a" and "an," as used herein the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

---

What is claimed is:

1. A NOD.Cg-Prkdc$^{scid}$ Il2rg$^{tm1wjl}$/SzJ (NOD scid gamma) mouse whose genome comprises
a human FLT3L transgene and
an inactivated mouse Flt3 allele.

2. The mouse of claim 1, wherein the mouse comprises a genomic modification that inactivates the mouse Flt3 allele.

3. The mouse of claim 2, wherein the genomic modification is in at least one region of the mouse Flt3 allele selected from coding regions, non-coding regions, and regulatory regions.

4. The mouse of claim 3, wherein the genomic modification is in at least one coding region of the mouse Flt3 allele.

5. The mouse of claim 4, wherein the genomic modification is in exon 6, exon 7, and/or exon 8.

6. The mouse of claim 2, wherein the genomic modification is selected from genomic deletions, genomic insertions, genomic substitutions, and combinations thereof.

7. The mouse of claim 6, wherein the genomic modification is a genomic deletion.

8. The mouse of claim 7, wherein the mouse Flt3 allele comprises a genomic deletion of nucleotide sequences in exon 6, exon 7, and exon 8.

9. The mouse of claim 8, wherein the nucleic acid sequence of SEQ ID NO: 5 has been deleted from the mouse Flt3 allele.

10. The mouse of claim 9, wherein the modified mouse Flt3 allele comprises the nucleic acid sequence of SEQ ID NO: 6.

11. The mouse of claim 1, wherein the human FLT3L transgene comprises a nucleic acid sequence of SEQ ID NO: 7.

12. The mouse of claim 1, wherein the mouse expresses human FLT3L.

13. The mouse of claim 1, wherein the mouse does not express a detectable level of mouse FLT3 and/or lacks a detectable number of CD135$^+$ multipotent progenitor cells.

14. The mouse of claim 1 further comprising human CD34$^+$ hematopoietic stem cells and/or a population of human CD45$^+$ cells.

15. The mouse of claim 14, wherein the population of human CD45+ cells comprises human CD45$^+$/CD3$^+$ T cells and/or human CD45$^+$/CD33$^+$ myeloid cells.

16. The mouse of claim 1, wherein the mouse exhibits mucosal engraftment of human CD45$^+$ cells in the small intestines of the mouse.

17. A method comprising sublethally irradiating the mouse of claim 1, and injecting the mouse with human CD34$^+$ hematopoietic stem cells.

18. A method comprising:
injecting a pronucleus of a NOD.Cg-Prkdc$^{scid}$ Il2rg$^{tm1wjl}$/SzJ (NOD scid gamma (NSG)) mouse with a nucleic acid encoding human FLT3L, producing a NSG Tg(Hu-FLT3L) mouse, and inactivating a mouse Flt3 allele in the NSG Tg(Hu-FLT3L) mouse; or
inactivating a mouse Flt3 allele in a NOD.Cg-Prkdc$^{scid}$ Il2rg$^{tm1wjl}$/SzJ (NOD scid gamma) mouse to produce a NSG Flt3$^{null}$ mouse, and injecting a pronucleus of the NSG Flt3$^{null}$ mouse with a nucleic acid encoding human FLT3L to produce a NSG Flt3$^{null}$ Tg(Hu-FLT3L) mouse.

19. A NOD.Cg-Prkdc$^{scid}$ Il2rg$^{tm1wjl}$/SzJ cell comprising a nucleic acid encoding human FLT3L and an inactivated endogenous Flt3 allele.

20. A transgenic rodent comprising the cell of claim 19, optionally wherein the transgenic rodent is a transgenic mouse.

* * * * *